United States Patent
Klintenstedt et al.

(10) Patent No.: US 10,898,646 B2
(45) Date of Patent: Jan. 26, 2021

(54) CONTAINER HOLDER ASSEMBLY

(71) Applicant: SHL Group AB, Nacka Strand (SE)

(72) Inventors: Per Klintenstedt, Nacka Strand (SE); Anders Wieselblad, Stockholm (SE); Gunnar Elmen, Huddinge (SE)

(73) Assignee: SHL Medical AG, Zug (CH)

( * ) Notice: Subject to any disclaimer, the term of this patent is extended or adjusted under 35 U.S.C. 154(b) by 516 days.

(21) Appl. No.: 15/142,887

(22) Filed: Apr. 29, 2016

(65) Prior Publication Data

US 2017/0312173 A1 Nov. 2, 2017

(51) Int. Cl.
*A61M 5/20* (2006.01)
*A61M 5/315* (2006.01)
(Continued)

(52) U.S. Cl.
CPC .......... *A61M 5/2033* (2013.01); *A61M 5/008* (2013.01); *A61M 5/315* (2013.01);
(Continued)

(58) Field of Classification Search
CPC ........ A61J 1/16; A61M 5/008; A61M 5/2033; A61M 5/315; A61M 5/31501;
(Continued)

(56) References Cited

U.S. PATENT DOCUMENTS 3,880,163 A * 4/1975 Ritterskamp ....... A61M 5/2033
604/136
5,226,895 A 7/1993 Harris
(Continued)

FOREIGN PATENT DOCUMENTS

CN 102869399 A 1/2013
CN 104321102 A 1/2015
(Continued)

OTHER PUBLICATIONS

International Search Report issued in International Application No. PCT/EP2017/057230 dated Jul. 12, 2017.
(Continued)

*Primary Examiner* — Jenna Zhang
(74) *Attorney, Agent, or Firm* — McDonnell Boehnen Hulbert & Berghoff LLP

(57) ABSTRACT

According to aspects of the present disclosure, a retaining apparatus for use with a medicament delivery device is provided. The medicament delivery device includes a container holder assembly and an actuator assembly. The container holder assembly is configured to receive a container containing a medicament. The container holder assembly is configured to couple to the actuator assembly. The actuator assembly includes a plunger rod for engaging a stopper in the container. The retaining apparatus includes a plunger lock, a retaining member, and a biasing member. The plunger lock is seated within a proximal end of the actuator assembly, and secures the plunger rod. The retaining member is seated within the plunger lock. The biasing member is secured between the proximal end of the actuator assembly and the retaining member. The retaining member is biased in a proximal direction by the biasing member.

17 Claims, 21 Drawing Sheets

(51) Int. Cl.
*A61M 5/00* (2006.01)
*A61J 1/16* (2006.01)

(52) U.S. Cl.
CPC ............ *A61M 5/31501* (2013.01); *A61J 1/16* (2013.01); *A61M 2005/31508* (2013.01)

(58) Field of Classification Search
CPC .......... A61M 2005/31508; A61M 5/24; A61M 5/31566; A61M 5/31576; A61M 2005/2485
See application file for complete search history.

(56) References Cited

U.S. PATENT DOCUMENTS

| | | | |
|---|---|---|---|
| 9,649,443 | B2 | 5/2017 | Klintenstedt et al. |
| 2004/0035491 | A1 | 2/2004 | Castellano |
| 2007/0005021 | A1 | 1/2007 | Kohlbrenner et al. |
| 2007/0021718 | A1 | 1/2007 | Burren et al. |
| 2009/0259181 | A1* | 10/2009 | Moser ................. A61M 5/2448 604/135 |
| 2011/0251553 | A1* | 10/2011 | Ratjen ................. A61M 5/2066 604/89 |
| 2013/0220869 | A1 | 8/2013 | Klintenstedt et al. |
| 2013/0226082 | A1 | 8/2013 | Klintenstedt et al. |
| 2013/0310757 | A1* | 11/2013 | Brereton ............ A61M 5/3157 604/197 |
| 2016/0193414 | A1* | 7/2016 | McLoughlin ....... A61M 5/3204 604/192 |
| 2016/0367763 | A1* | 12/2016 | Tschirren ............ A61M 5/3157 |
| 2017/0304548 | A1* | 10/2017 | Chen .................... A61M 5/3202 |

FOREIGN PATENT DOCUMENTS

| | | |
|---|---|---|
| GB | 743839 | 1/1956 |
| TW | 201219080 A1 | 5/2012 |
| WO | WO 95/21645 | 8/1995 |
| WO | WO 96/17640 | 6/1996 |
| WO | WO 2008/074897 A1 | 6/2008 |
| WO | WO 2009/101005 A1 | 8/2009 |
| WO | 2010000559 A1 | 1/2010 |
| WO | WO 2010/043533 A1 | 4/2010 |
| WO | 2012064258 A1 | 5/2012 |
| WO | 2012/173553 A1 | 12/2012 |
| WO | WO 2013/085453 A1 | 6/2013 |
| WO | 2014/139839 A1 | 9/2014 |
| WO | 2015/018578 A1 | 2/2015 |
| WO | 2016055295 A1 | 4/2016 |
| WO | WO-2016055295 A1 * | 4/2016 |

OTHER PUBLICATIONS

Search Report issued in Taiwanese Patent Application No. 106113803 dated Nov. 29, 2017.
Chinese Office Action for CN App. No. 201780024946.3, dated Jul. 15, 2020.

* cited by examiner

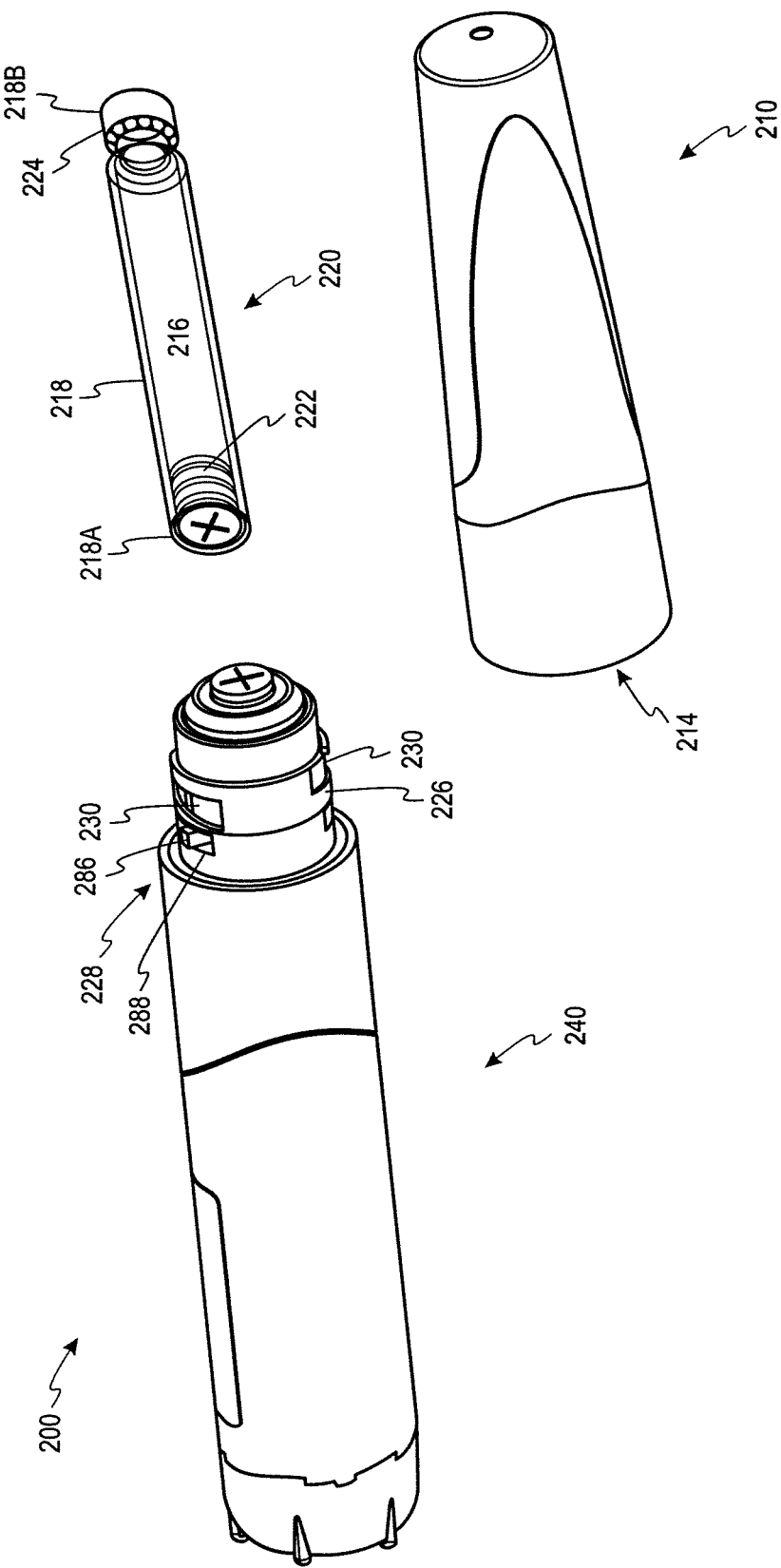

CONTAINER HOLDER ASSEMBLY

BACKGROUND

A medicament delivery device, such as an injector, is often arranged with a container holder to allow operations to be carried out on the container, for instance displacement within the injector housing during skin penetration, expulsion of medicament by a plunger acting on the stopper in the container, penetration of the septum using a needle and replacement of container. Because of tolerances, manufactured containers vary in size, which may result in the position of the container within the holder being somewhat affected during handling of the device. For instance, displacement of the container may occur as a result of penetrating the septum of the container with a needle or by sudden impact forces to the housing of the device. If the container is not exactly positioned in relation to the holder, the stroke length of the plunger rod—and consequently the dosage set by the user or the manufacturer of the device—will not be exactly correlated to the actual position of the container, resulting in the wrong dose being delivered. Also, movement of the container within the holder may lead to a higher risk of breaking the container due to impact forces between the holder and the container.

SUMMARY

According to aspects of the present disclosure, a retaining apparatus for use with a medicament delivery device is provided. The medicament delivery device includes a container holder assembly and an actuator assembly. The container holder assembly is configured to receive a container containing a medicament. The container holder assembly is configured to couple to the actuator assembly. The actuator assembly includes a plunger rod for engaging a stopper in the container. The retaining apparatus includes a plunger lock, a retaining member, and a biasing member. The plunger lock is seated within a proximal end of the actuator assembly, and secures the plunger rod. The retaining member is seated within the plunger lock. The biasing member is secured between the proximal end of the actuator assembly and the retaining member. The retaining member is biased in a proximal direction by the biasing member.

The present disclosure thus provides a device that can securely keep the container in a predetermined position in relation to the container holder in order to be able to deliver a set dose in a safe and reliable way without damaging the holder or the container. With regard to cost and complexity the device can be easy to manufacture and to implement. The resulting device can also be simple and intuitive for the end user to operate.

These as well as other aspects, advantages, and alternatives will become apparent to those of ordinary skill in the art by reading the following detailed description with reference where appropriate to the accompanying drawings. Further, it should be understood that the description provided in this summary section and elsewhere in this document is intended to illustrate the claimed subject matter by way of example and not by way of limitation.

BRIEF DESCRIPTION OF THE DRAWINGS

In the following description of embodiments of the present disclosure, reference will be made to the accompanying drawings of which:

FIGS. 8A-8B are perspective views of a medicament delivery device in a disassembled state according to additional aspects of the present disclosure.

DETAILED DESCRIPTION

Embodiments of the present disclosure will now be described in detail. As should be noted in the present application, when the term "distal part/end" is used, this refers to the part/end of the delivery device, or the parts/ends of the members thereof, which is/are located the furthest away from the medicament delivery site of the patient. Correspondingly, when the term "proximal part/end" is used, this refers to the part/end of the delivery device, or the parts/ends of the members thereof, which, is/are located closest to the medicament delivery site of the patient.

According to an aspect of the present disclosure, a container holder assembly is provided for use in a medicament delivery device, which container holder assembly comprises a tubular body elongated in an axial direction, said tubular body having a proximal end and an opposite distal end. A retaining member is releasably arranged to said tubular body for securing an elongated container placed inside the tubular body. The retaining member comprises a resilient structure that is capable of exerting an axial force on said container in said tubular body for holding the container in a fixed position inside the tubular body and thereby avoiding breakage or displacement of the container.

Figure 1:
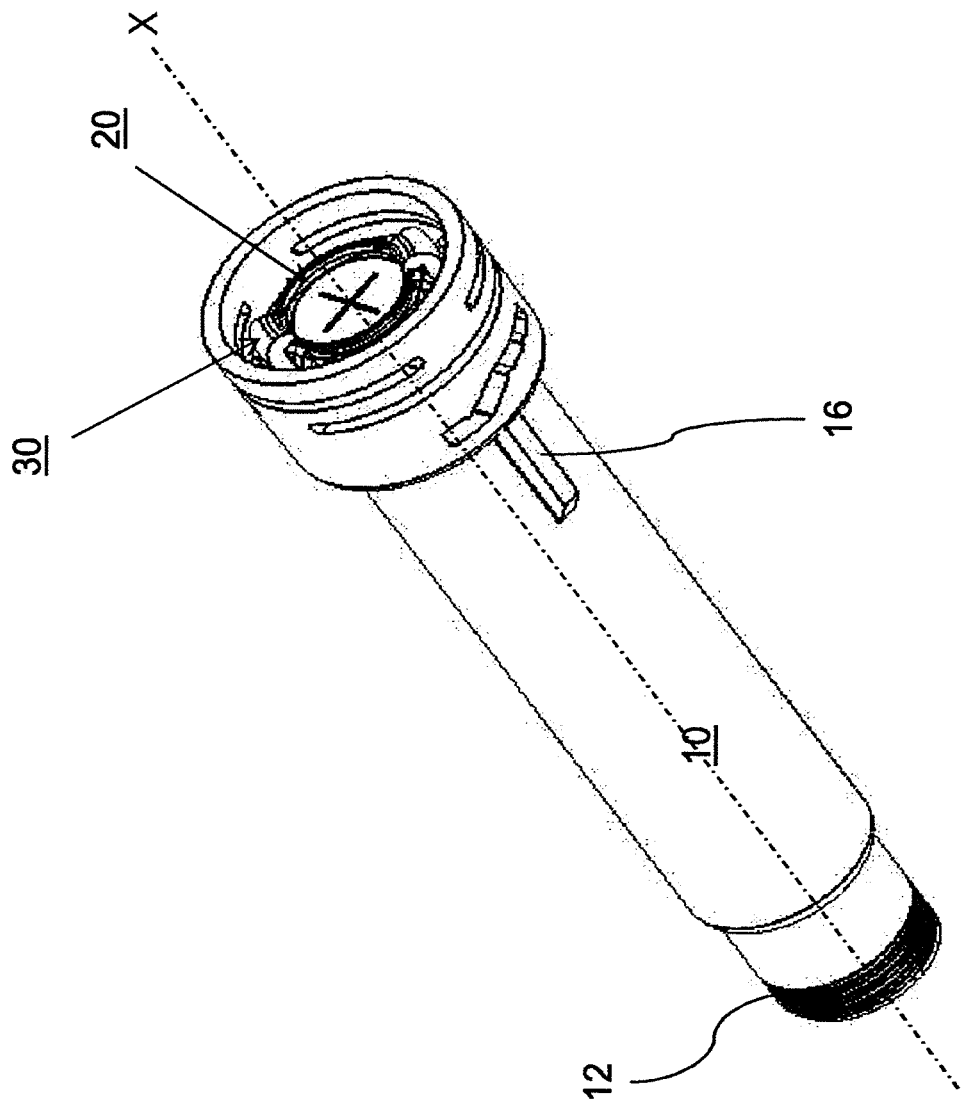
FIG. 1 is a perspective view of a container holder assembly and container in an assembled state according to aspects of the present disclosure.

FIGS. 1-4 depict an example container holder assembly according to such aspects of the present disclosure. The example shown in the FIGS. 1-4 is a container holder assembly for medicament delivery devices but is not restricted to it. FIG. 1 is a perspective view of exemplary components of such a container holder assembly. A tubular body 10, such as a container holder, is elongated along an axis X with a closed proximal end and an open distal end for receiving a container 20. In order to secure the container 20 inside the tubular body 10, a retaining member 30 is arranged to the container holder for gripping the container and resiliently urging it into abutment with a stop surface inside the tubular body 10.

The exemplary embodiment disclosed in FIG. 1 shows the retaining member 30 arranged at the open, distal end of the tubular body 10, gripping the distal end of the container 20. The present disclosure is not restricted to this arrangement however. The container holder assembly may be may be constructed in many different ways without departing from the concept of the present disclosure. The resilient structure of the retaining member 30 will be explained below.

The tubular body 10 may also be arranged with radially protruding elements 16 arranged to key the container holder assembly to a certain type of delivery device in order to prevent the use of the assembly in a device that it is not intended for.

A proximal part of the tubular body 10 may be arranged with an interface 12, such as threads, for connecting a delivery member (not shown). The delivery member may be a needle, a nozzle, a mouth piece, or the like.

Figure 2:
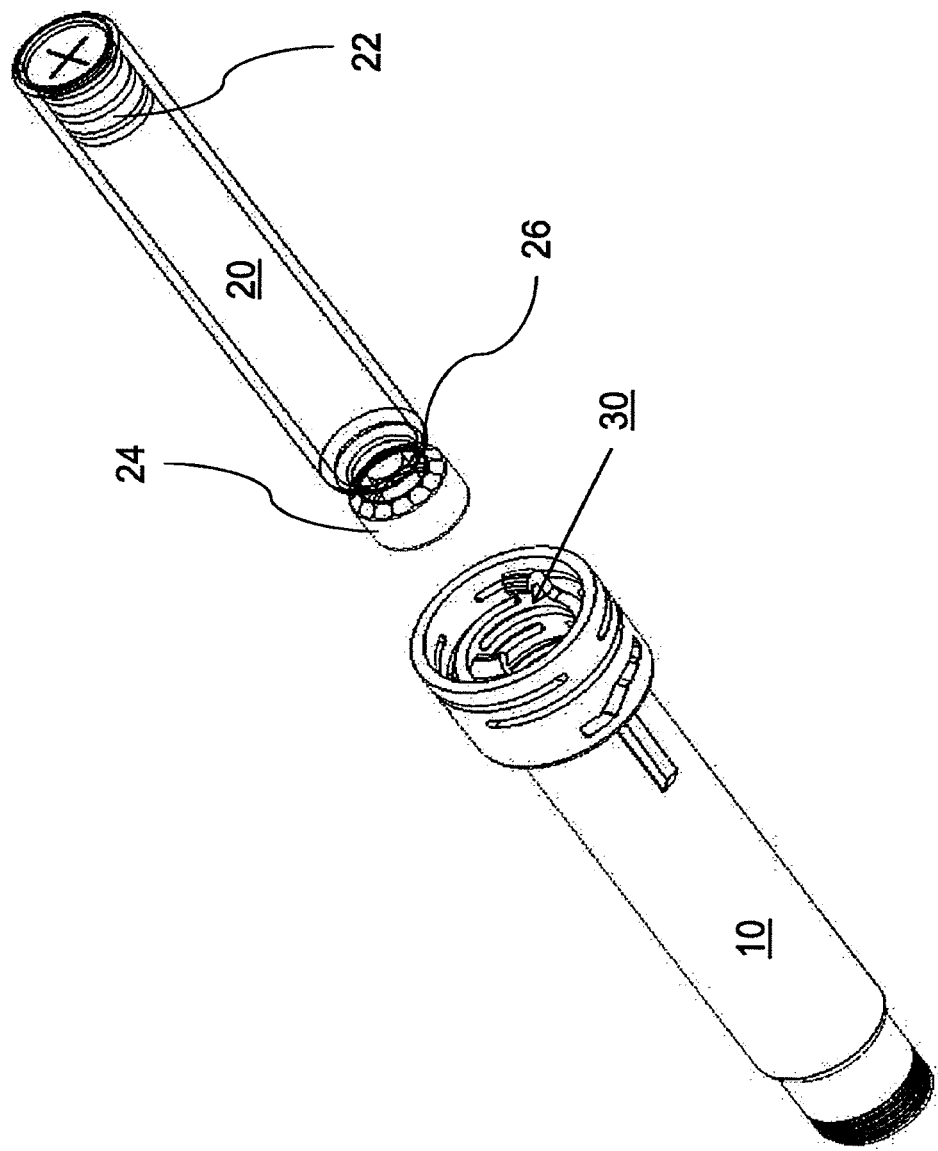
FIG. 2 is a perspective view showing a container outside the container holder assembly.

FIG. 2 shows the assembly in a semi-assembled state, wherein the container 20 has not yet been loaded in the tubular body 10 and wherein the retaining member 30 is loosely arranged to the tubular body 10, prepared for receiving the container 20. The physical dimensions of the assembly are adapted to a certain type of container but the present disclosure allows for large dimensional tolerances of the containers thanks to the resilient structure of the retaining member 30, which holds the container in a predetermined position inside the container holder despite variations in physical dimensions of the container.

An exemplary container 20, as show in FIG. 2, may contain medicament and is tubular and made of glass. A proximal end typically has a shoulder portion 26 connecting the tubular part with a neck portion and a cap 24. The cap comprises a septum that seals the proximal end of the container. The distal end of the container is sealed by an axially movable stopper 22.

Figure 3:
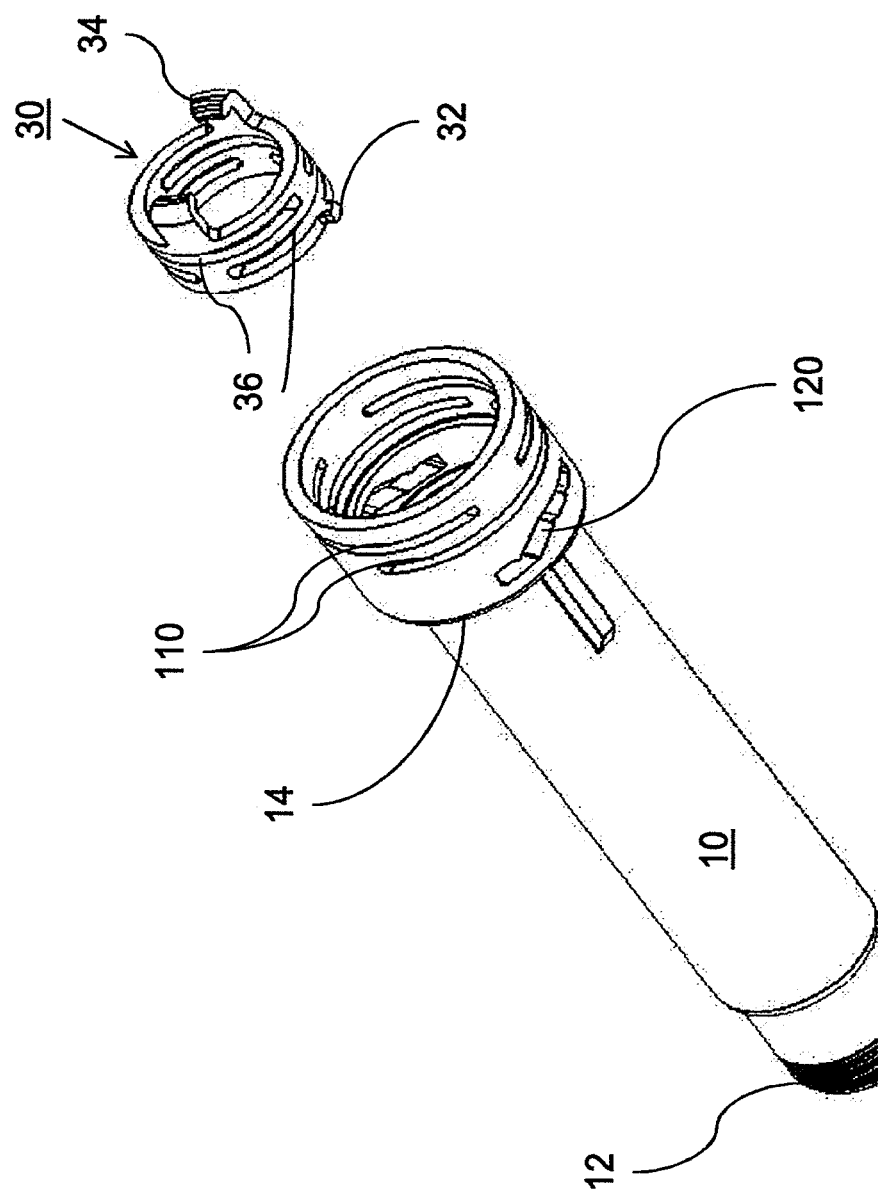
FIG. 3 is a perspective view showing the container holder assembly in a disassembled state.

FIG. 3 depicts a perspective view showing the container holder assembly in a disassembled state. The retaining member 30, which is here shown outside the tubular body 10, comprises a resilient structure that allows the body of the retaining member to be flexible in the axial direction, i.e. to stretch or to compress, so that the proximal end and the distal end of the retaining member may be axially displaced with regard to each other. The resilient structure 36 is achieved by forming circumferentially elongated cut-outs, or slits, in the tubular wall of the retaining member 30. The slits are arranged in at least two parallel circumferentially aligned rows, wherein a space between any two slits of one row is aligned with the centre of a slit of an adjacent row.

At least two gripping means 34 are arranged on the distal annular end surface of the retaining member 30. The gripping means 34 may be formed as distally protruding, inwardly curved hooks that are able to flex radially outwards as the container 20 is pushed inside the tubular body 10. Each gripping means is aligned with the centre of one of the most distal slits.

The proximal portion of the retaining member 30 is arranged with a first locking means 32 capable of mutual mechanical connection with a second locking means 120 of the tubular body 10. The first locking means 32 may be formed as at least two protrusions, or guide knobs, that extend radially outwardly from the outer circumferential surface of the retaining member 30, whereas the second locking means 120 may be formed as a cut-out, or guide track, that is able to guide a protrusion of the first locking means 32 along the track as the first and second locking means are axially rotated in relation to each other, i.e. in the fashion of a bayonet connection. Each protrusion is aligned with the centre of one of the most proximal slits.

The gripping means 34 are arranged to abut the distal annual end surface of the container 20 when the container has been placed in the tubular body 10 and the first and second locking means are brought into locking position with each other (explained in detail below).

The resiliency of the retaining member 30 of the exemplary embodiment of FIG. 3 results from the careful alignment of the slits, the gripping means 34 and the first locking means 32. For best performance, the number of gripping means equals the number of slits in the most distal row of slits and the number of first locking means equals the number of slits in the most proximal row of slits. Preferably, the number of slits in one row equals the number of slits in each of the other rows. Most preferably, the number of slits in one row equals two. To achieve good resiliency it is also preferable that the circumferential length occupied by a slit is significantly larger than the circumferential length occupied by the space between two slits of any adjacent rows.

Figure 4:
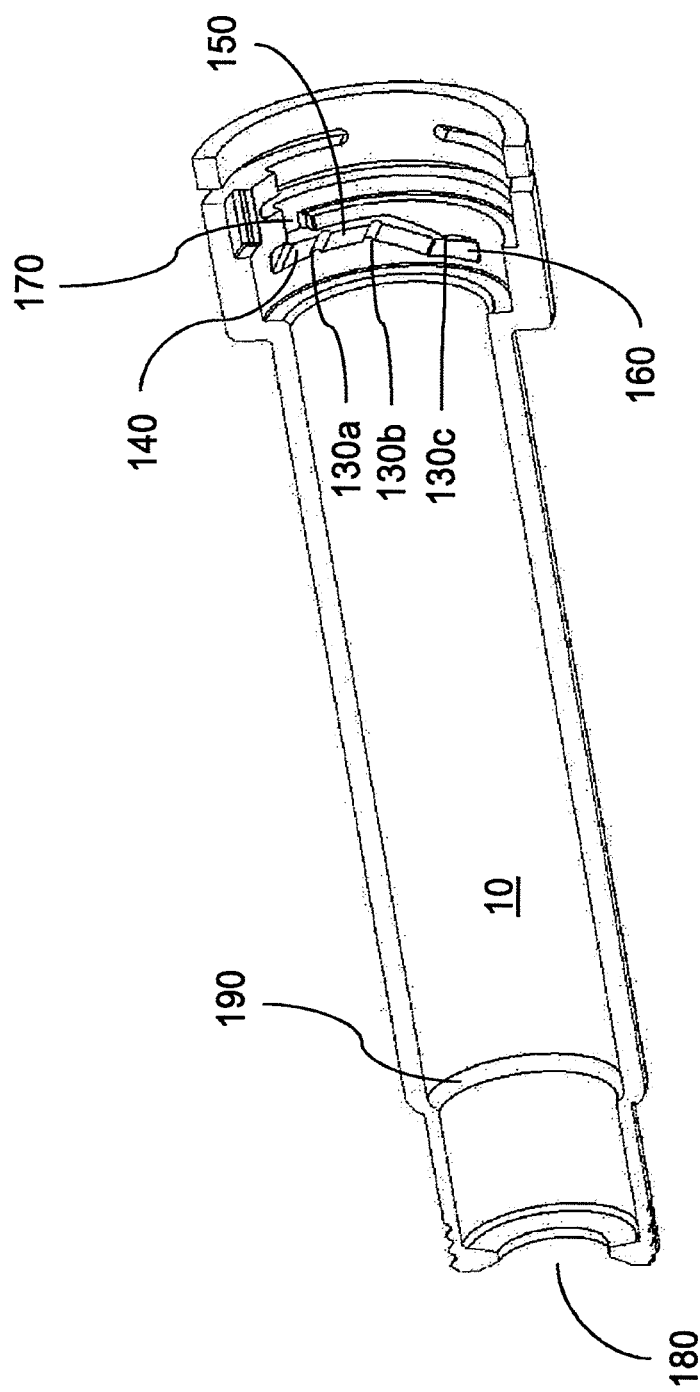
FIG. 4 is a cross-sectional view of the container holder assembly and the container of FIG. 1.

In a similar fashion, an end—preferably the distal end—of the tubular body 10 may be arranged with a second resilient structure 110. As the container holder assembly, with a container inside, is inserted by a user in a delivery device by attaching the tubular body to holding means (not shown) arranged at a proximal receiving end of the device (not shown). The distal annular end surface of the tubular body thereby comes into abutment with a surface of the delivery device, forcing the second resilient structure 110 to compress axially. The user may then attach a delivery member to the interface 12 in order to use the device FIG. 4 shows a cross-section of the exemplary embodiment of the tubular body 10. The second locking means 120 (FIG. 2) may be formed as a cut-out, or guide track, that is able to guide a protrusion of the first locking means 32 along the track as the first and second locking means are axially rotated in relation to each other. The track has a distally directed opening 170 through which the first locking means 32 of the retaining member 30 may be inserted into the track. After insertion the first locking means is in the initial position 140 of the second locking means. By slightly rotating the tubular body 10 and the retaining member 30 with respect to each other, for instance by using a specialized tool, the first locking means is forced past a first stopper 130a arranged to prevent unintentional rotation of the locking means. The first locking means is then in a loading position 150, as depicted in FIG. 2. In the loading position 150 the container holder assembly is ready for insertion of a container 20 into the tubular body 10. As the container is pushed into the tubular body the gripping means 34 flex radially outwards, snapping back as the distal end of the container passes the gripping means. The container is now loosely secured in the tubular body, resting with its shoulder portion 26 against the inner annular ledge 190 of the tubular body 10. The container will not fall out since the gripping means 34 is blocking movement in the distal direction and the first locking means 32 is confined between the first stopper 130a and a second stopper 130b. However, in the loading position, the retaining member still does not exert an axial force on the container.

To achieve an object of the present disclosure, i.e. to fix the container in an exact predetermined position in the tubular body 10, an axial force can be exerted between the tubular body and the container, such that they are pressed towards each other. In the exemplary embodiment of FIG. 4 this is attained by further rotation of the retaining member with regard to the tubular body. When the first locking means 32 is forced past the second stopper 130b the track of the second locking means deviates from a circumferential path to a circumferential/axial path, forcing the proximal part, i.e. the first locking means and consequently the whole the retaining member in a proximal, axial direction. Since the gripping means 34 is arranged to abut the distal annular surface of the container 20 and the container is hindered from proximal displacement because it is resting with its shoulder portion 26 in abutment with the inner annular ledge 190 of the tubular body 10, the resilient structure 36 begins to stretch axially in the proximal direction. The tensioned resilient structure exerts an axial force such that the gripping means 34 urges the shoulder portion 26 of the container 20 and the inner annular ledge 190 of the tubular body 10 against each other.

As the retaining member and the tubular body are further rotated with regard to each other, the track of the second locking means 120 eventually returns to a circumferentially aligned path. The first locking means is forced past the third stopper 130c and comes to rest in a holding position 160, abutting the distal surface of the track due to the axial force exerted by the resilient structure 36.

The overall pitch of the track of the second locking means is carefully determined during manufacture of the assembly to achieve a force that is strong enough to fix the container inside the tubular body, regardless of the tolerances of the container used, but at the same time to achieve a force that is not so strong as to risk damaging the container.

Another parameter that may be used to calibrate the force during manufacturing is the resiliency of the resilient structure 36. This may be varied, for instance by selecting an appropriate number of rows of slits of the resilient structure, or by the material chosen for the container holder assembly, or by the thickness of the wall of the retaining member or the distance between the rows of slits, etc.

Other designs of the locking means 32, 120 are also conceivable, such as mutually engaging threads.

Figure 5:
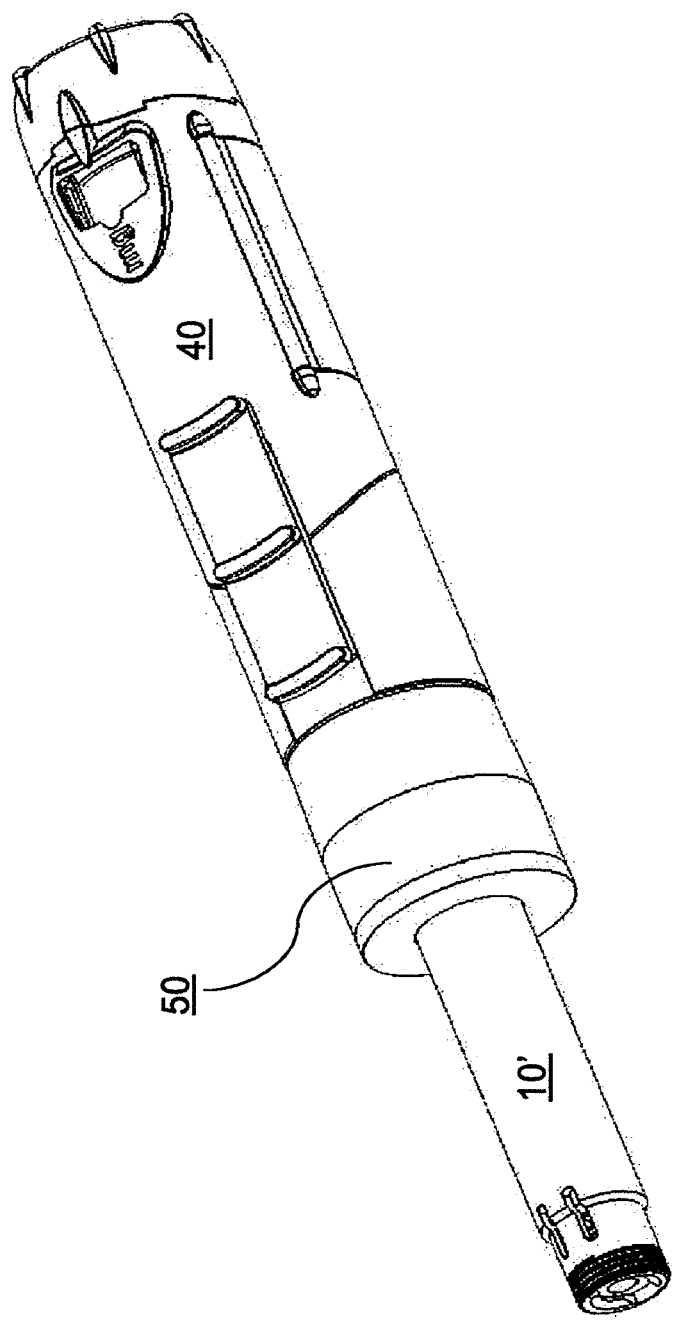
FIG. 5 is a perspective view of a medicament delivery device according to additional aspects of the present disclosure.
Figure 6:
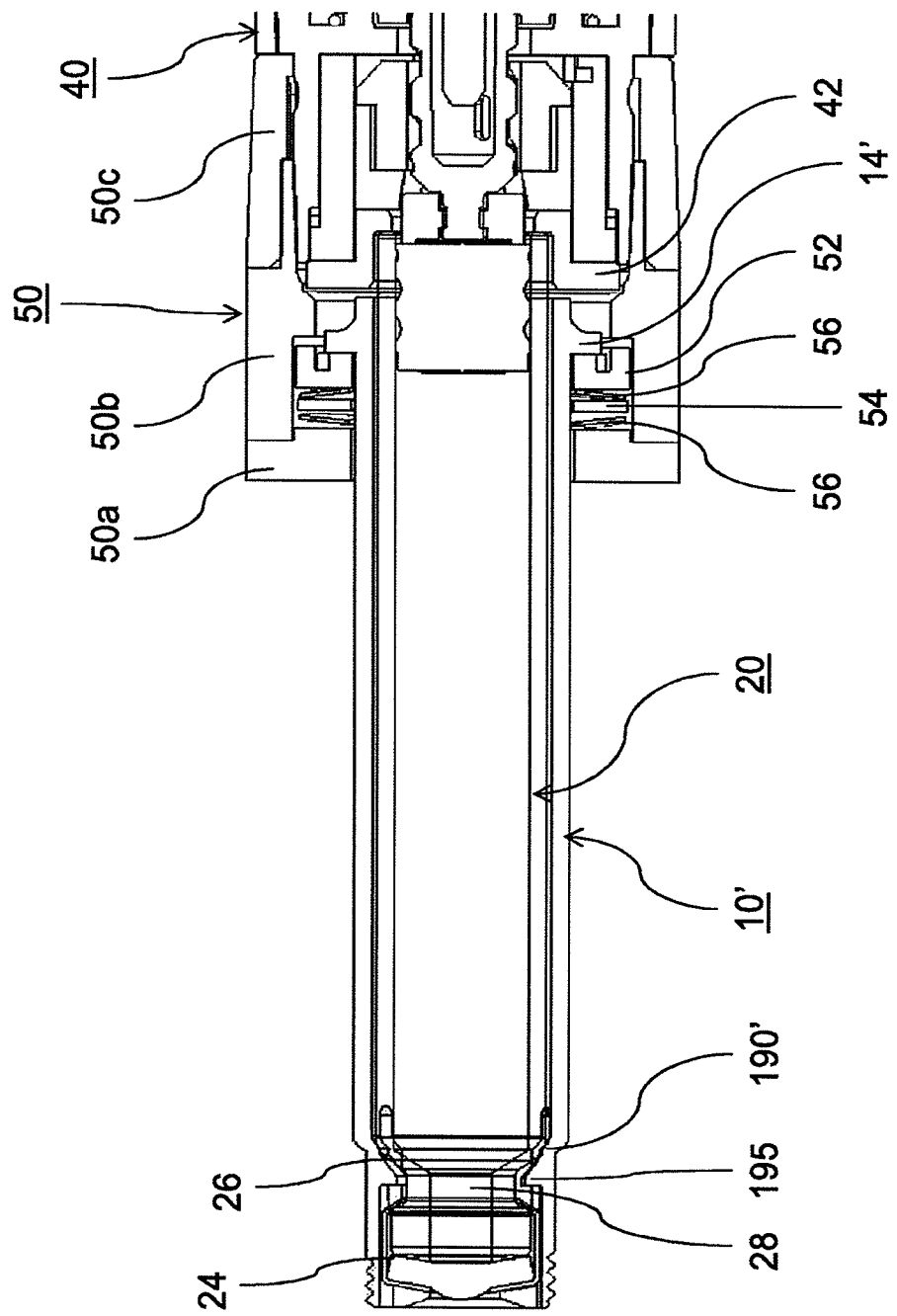
FIG. 6 is a cross-sectional view of the medicament delivery device of FIG. 5.
Figure 7:
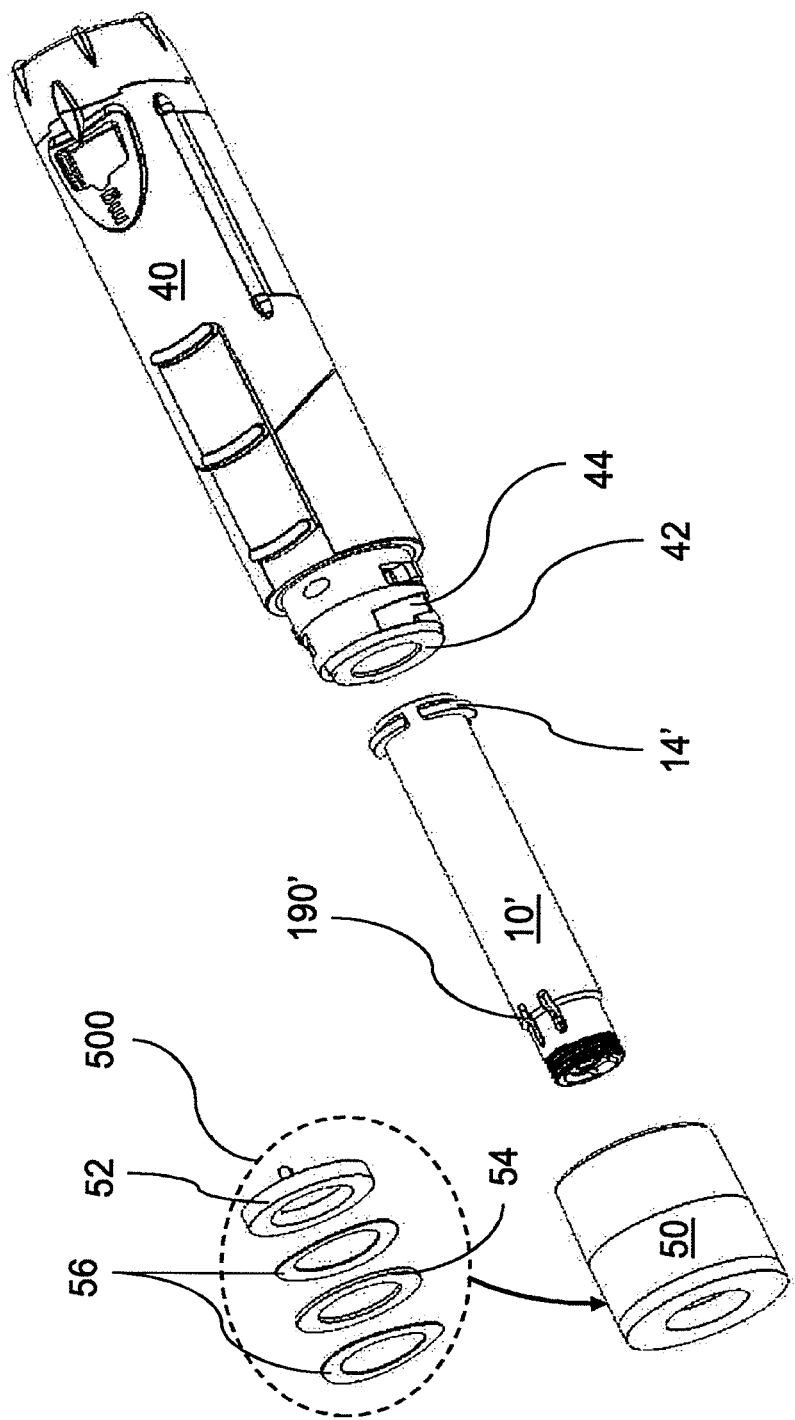
FIG. 7 is an exploded perspective view of the medicament delivery device of FIG. 5.

A second exemplary embodiment of the present disclosure is shown in FIGS. 5-7. FIG. 5 is a perspective view of a medicament delivery device 40 to which a container holder 10', comprising a container (not shown), has been attached using retaining member 50.

FIG. 6 shows a cross-section of the connection between the device 40 and the container holder 10' of FIG. 5. The retaining member 50 is, in the exemplary embodiment shown, comprised of a first part 50a, a second part 50b and a third part 50c that together form an axially aligned annular housing with a through-going axially aligned hole for accommodating the container holder 10' with the container 20. The retaining member 50 also houses a resilient structure 500 comprising at least one resilient washer 56, and a spacer 52. If multiple resilient washers 56 are used, at least one supporting washer 54 is positioned between them in order to separate the resilient washers 56 from each other.

The third part 50c of the retaining member comprises attachment means (not shown) on a distal circumferential surface for mutually connecting with engagement means 44 on a proximal circumferential surface of the delivery device 40. Various solutions are conceivable for the mutual connection of the retaining member and the delivery device, e.g. such as a threaded connection or bayonet connection.

The retaining member 50 and its constituent components are assembled during manufacturing and are designed for a predetermined kind of container holder 10', which in turn is designed to hold a predetermined kind of container 20. An object of the present disclosure, however, is to allow large tolerances in the physical dimensions of the container 20 without affecting the accuracy of the dose delivery, i.e. by holding the container in a fixed position in relation to the container holder, and without damaging the container. This is achieved by resilient fixation of the container in the holder.

The function of the retaining member 50 will now be described in conjunction with FIG. 7, which is an exploded view of the delivery device 40 and the container holder assembly, i.e. the retaining member 50 and the container holder 10'. Also shown is an inserted exploded image of the resilient structure 500 housed in the resilient means 50.

The resiliency of the retaining member 50 is a function of the stack of resilient washers 56. The washers may, for instance, have a wavy shape that results in an axial restoring force if the washers are compressed. Since the shape of the individual resilient washers is identical a supporting washer 54 may be used to separate them from each other. Otherwise, adjacently packed resilient washers would result in much reduced flexibility.

When the delivery device is to be used a container is inserted in the tubular body 10' by the distal end. At least two radially inwardly protruding cut-outs in the form of flexible tongues 195 are arranged in the circumferential wall of the tubular body 10' to flex radially outwards as the cap 24 is pushed against the tongues in order to let the container pass. Thereafter, the tongues flex back inwards, preventing return-movement of the container and securing it by its neck portion 28 (FIG. 6) inside the tubular body 10' such that it cannot accidentally fall out before the container holder assembly has been attached to the delivery device 40. When the container is secured in the tubular body, the distal end of the container still protrudes distally of the tubular body, the function of which will be explained below.

The tubular body 10' holding the container is then inserted in the retaining member 50 from the distal side such that the proximal surface of the circumferential flange 14' arranged at the distal end of the tubular body comes to rest against the distal surface of the annular spacer 52. The container holder assembly, including the container, is subsequently attached to the proximal end of the delivery device by the mutual connection described above.

As the mutual connection of the container holder assembly and the delivery device is tightened, such as by turning the retaining member 50 in relation to the delivery device 40 for mutually engaging threads or for operating a bayonet connection, the protruding distal annular surface of the container abuts the stopping element 42. The abutting function of the stopping element could also be achieved by an integrated surface of the delivery member 40 itself, such as a surface of the housing.

Further tightening of the connection results in compression of the resilient washers 56 between the first part 50a and the spacer 52 resting against the flange 14'. This leads to a restoring axial force, arising from the compressed resilient washers 56, that acts on the flange 14' to urge the tubular body 10' in the distal direction. Since the container 20 abuts the stopping element 42, the inner annular ledge 190' is brought into abutment with the shoulder portion 26 of the container, forcing the container against the stopping element 42. The force arising from the compression of the resilient washers 56 thereby fixes the container with regard to the tubular body 10' and the delivery device 40.

Figure 8A:
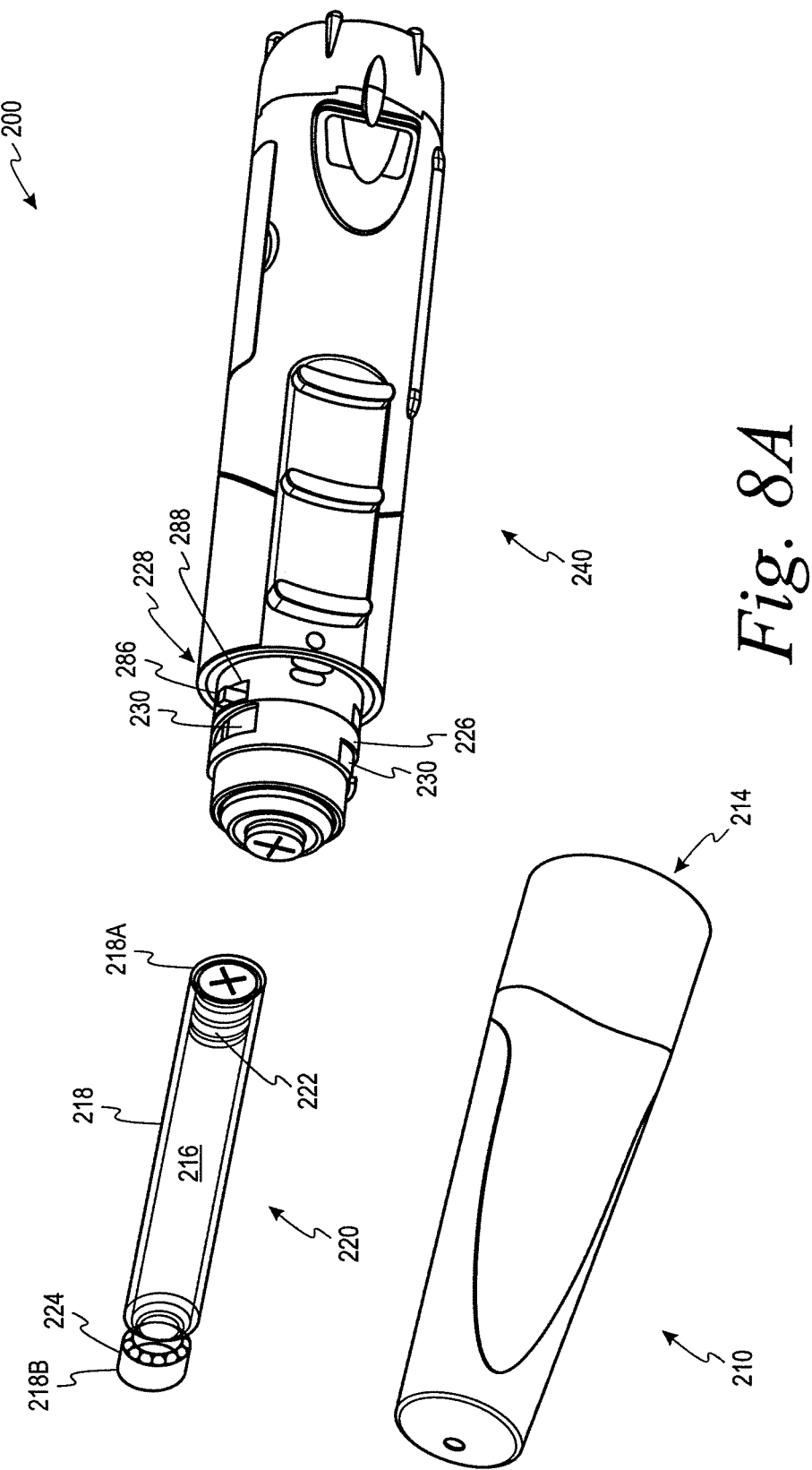
Figure 9A:
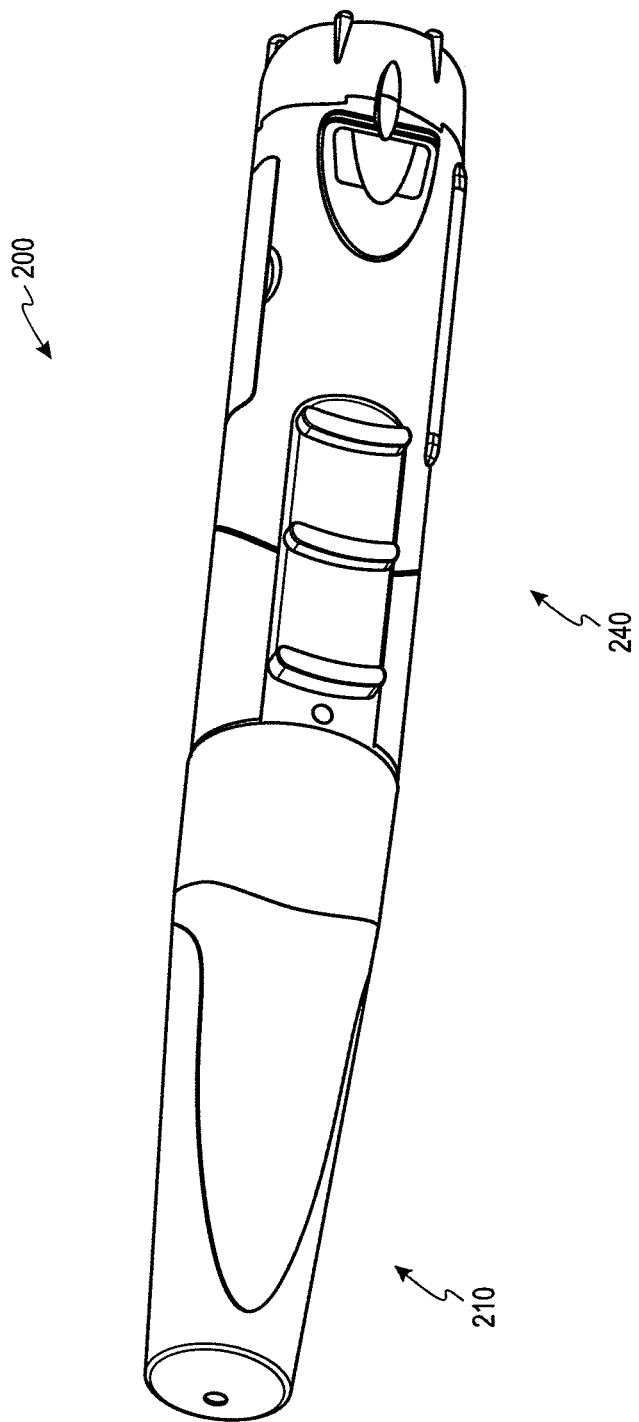
FIGS. 9A-9B are perspective views of the medicament delivery device of FIGS. 8A-8B in an assembled state.
Figure 9B:
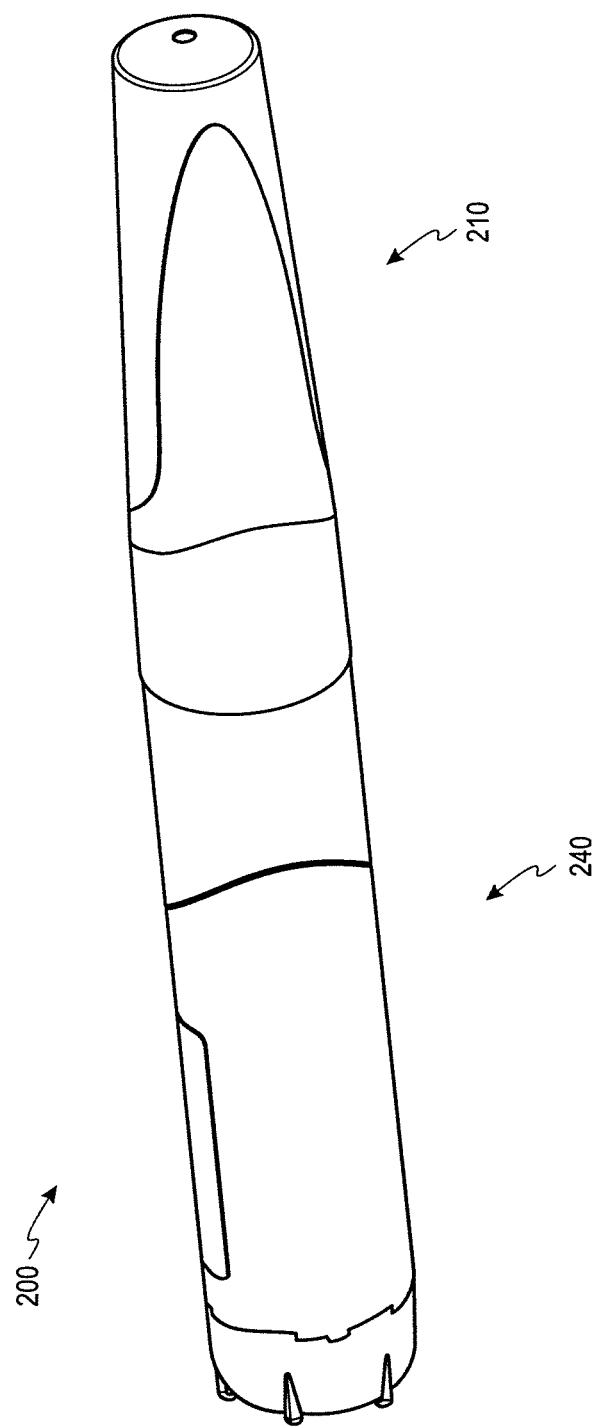

Referring now to FIGS. 8A-16B another example medicament delivery device 200 is shown according to aspects of the present disclosure. FIGS. 8A-8B depict perspective views of the medicament delivery device 200 in a disassembled state. As shown in FIGS. 8A-8B, the medicament delivery device 200 includes a container holder assembly 210, a container 220, and an actuator assembly 240. The container 220 contains a medicament (e.g., a liquid contents). The container holder assembly 210 includes a bore 214 for receiving the container 220. The actuator assembly 240 removably couples with the container holder assembly 210 and includes components that facilitate delivering one or more doses of a medicament from the container 220 to a patient. FIGS. 9A-9B depict perspective views of the medicament delivery device 200 with the container 220 in the container holder assembly 210 and the container holder assembly 210 coupled to the actuator assembly 240 (i.e., in an assembled state).

To contain the medicament, the container 220 can have an internal chamber 216 defined by elongated, hollow body 218 that is fluidly sealed on a distal end 218A and a proximal end 218B (e.g., as described above with respect to container 20). For example, the container 220 can be sealed by a cap 224 at the proximal end 218B. At the distal end 218A, the container 220 is fluidly sealed with an axially movable stopper 222 that engages an inner wall of the container 220. As the stopper 222 moves axially toward the proximal end 218B of the container 220, the stopper 222 pushes the medicament contents through an opening in the proximal end 218B, provided that the fluid seal (if included) on the proximal end 218B has been pierced, breached, or opened.

As noted above, the container holder assembly 210 can be removably coupled to the actuator assembly 240. For example, on an exterior surface 226 of a proximal portion 228, the actuator assembly 240 can include one or more tracks 230 that receive one or more corresponding protrusions 234 on an inner surface 236 of a distal portion 232 of the container holder assembly 210 (shown in FIGS. 10-11). The track(s) 230 can receive the protrusion(s) 234 via a distally directed opening and then guide the protrusion(s) 234 distally along a circumference of the exterior surface 226. As the container holder assembly 210 and the actuator assembly 240 are rotated with respect to one another, the protrusion(s) 234 travel along the track(s) 230 causing the container holder assembly 210 to move distally towards the actuator assembly 240 due to a distally directed pitch of the track(s) 230.

Figure 10:
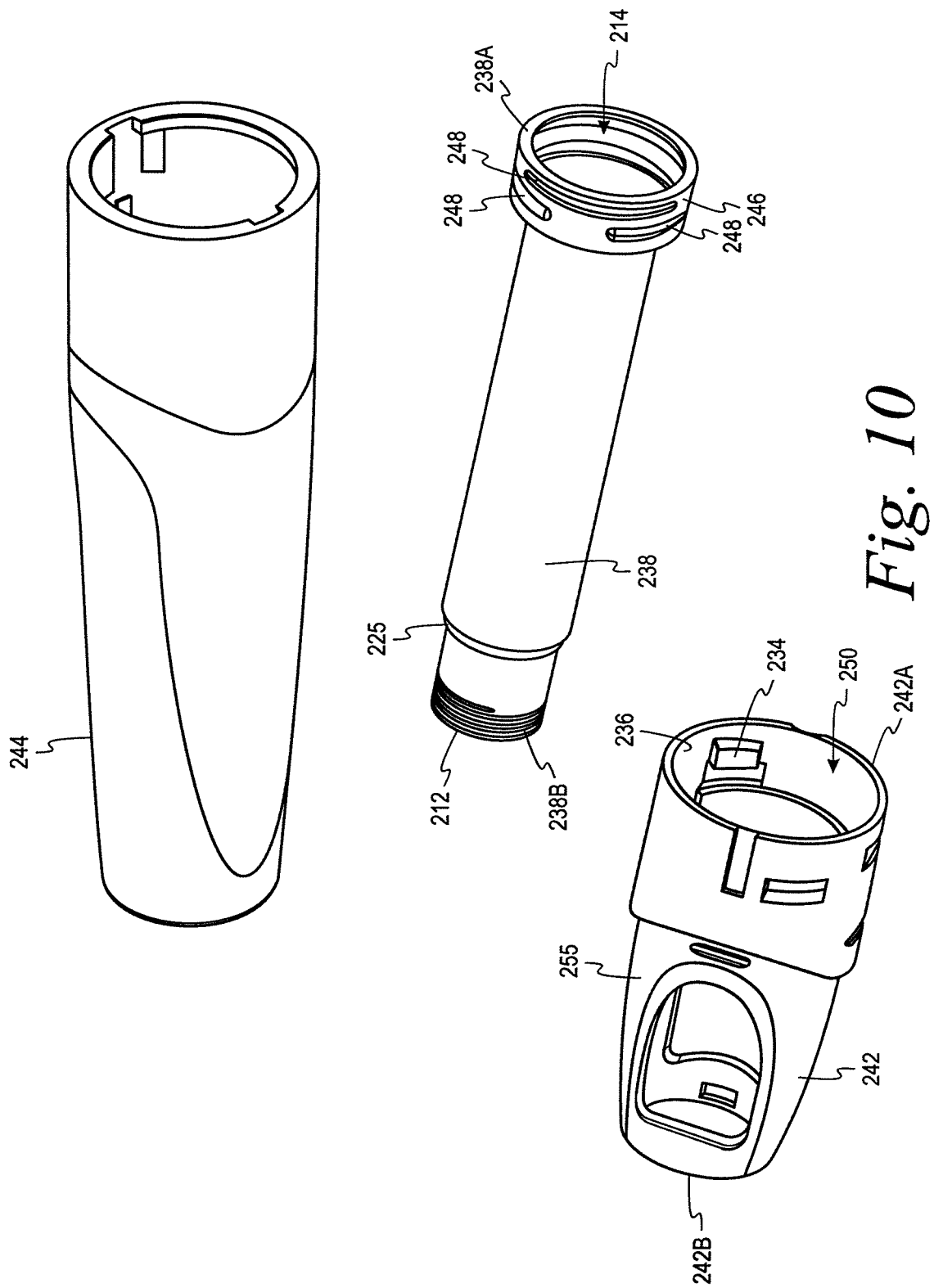
FIG. 10 is an exploded perspective view of a container holder assembly according to aspects of the present disclosure.
Figure 11:
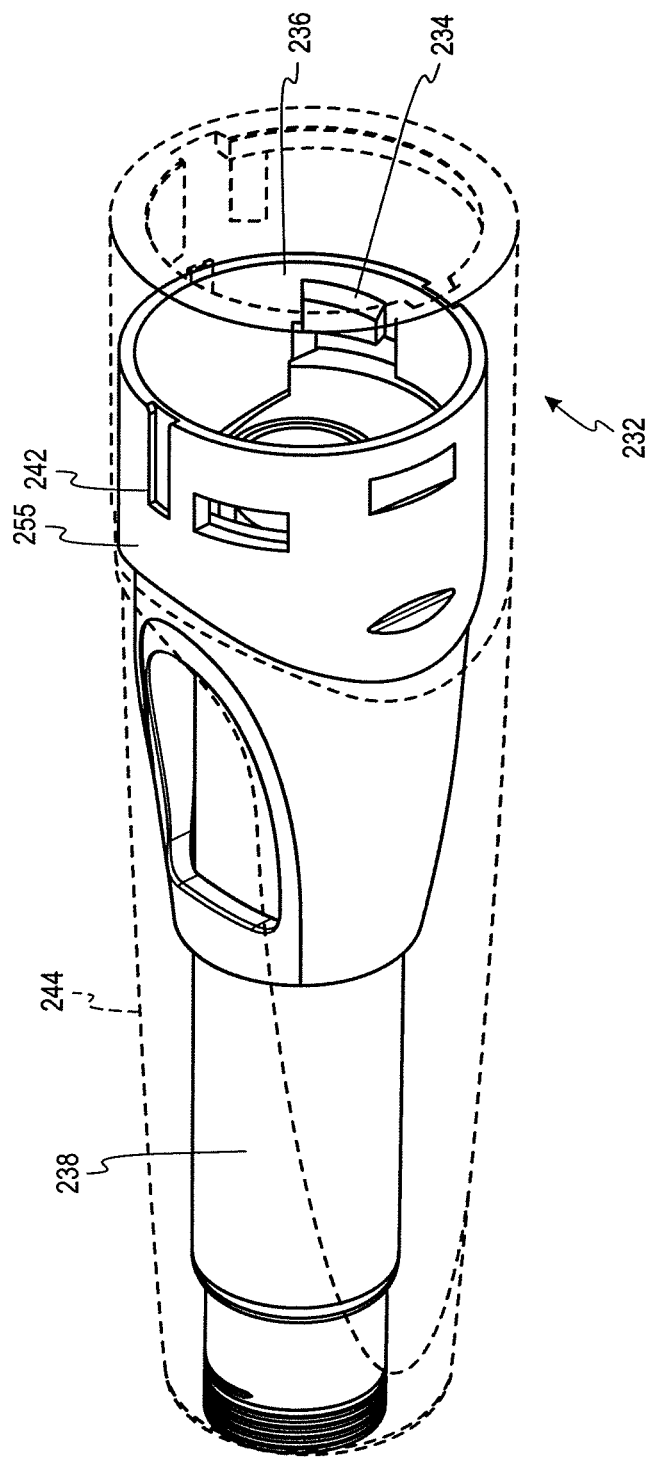
FIG. 11 is a perspective view of the container holder assembly of FIG. 10.

The container holder assembly 210 is further depicted in FIGS. 10-11. FIG. 10 depicts an exploded view of the container holder assembly 210. As shown in FIG. 10, the container holder assembly 210 includes an inner housing 238, an outer housing 242, and a cover 244. The inner housing 238 includes the bore 214 for receiving the container 220. The bore 214 extends from an open distal end 238A to an open proximal end 238B of the inner housing 238. The bore 214 may narrow at the proximal end 238B (e.g., at a shoulder portion 225) so as to axially retain the container 220 in the inner housing 238 at the proximal end 238B. Further, at the proximal end 238B, the inner housing 238 includes an interface 212 (e.g., threads). The interface 212 is configured to couple the inner housing 238 to a delivery member such as, for example, a needle, a nozzle, a mouth piece, and/or the like.

At the distal end 238A, the inner housing 238 includes a resilient structure 246. The resilient structure 246 includes one or more apertures 248. The aperture(s) 248 allow the resilient structure 246 to axially compress and/or stretch and, thus, provide resiliency to the resilient structure 246. In an example, the aperture(s) 248 of the resilient structure 246 can be formed as slits arranged in a plurality of rows. For instance, the slits can be arranged on the resilient structure 246 in a manner similar to that described above with respect to the slits on the retaining member 30 and the second resilient structure 110.

The outer housing 242 has an axial cavity 250 defined by the inner surface 236, which extends between openings at a distal end 242A and a proximal end 242B of the outer housing 242. When the container holder assembly 210 is assembled, the inner housing 238 is received in the cavity 250 of the outer housing 242. The outer housing 242 can be coupled to the inner housing 238 by, for example, a friction fit. As such, the cavity 250 can have a size and shape corresponding to a size and shape of the inner housing 238. In other examples, the outer housing 242 can be coupled to the inner housing 238 in additional or alternative ways (e.g., by locking tabs, threads, adhesives, etc.).

The cover 244 can be removably coupled to the outer housing 242. For example, the cover 244 can couple to the outer housing 242 via friction-fit, snap-fit, locking tabs, corresponding detents and recesses, etc. When coupled to the outer housing 242, the cover 244 can substantially enclose the inner housing 238 and the outer housing 242. In this way, the cover 244 can protect the container 220 in the container holder assembly 210 from contamination when not in use.

FIG. 11 depicts the container holder assembly 210 in the assembled state. In FIG. 11, the cover 244 is shown in broken lines to show the inner housing 238 and the outer housing 242 within the cover 244. As shown in FIG. 11, the inner housing 238 is received in the outer housing 242. The outer housing 242 further includes one or more protrusions 234 extending from the inner surface 236 in a distal portion of the outer housing 242. The protrusions 234 are configured to engage with corresponding tracks 230 on the delivery device 240, as described herein. At a proximal portion, the outer housing 242 includes an outer surface 255 to which the cover 244 couples when the container holder 210 is received in an internal cavity of the cover 244.

Figure 12:
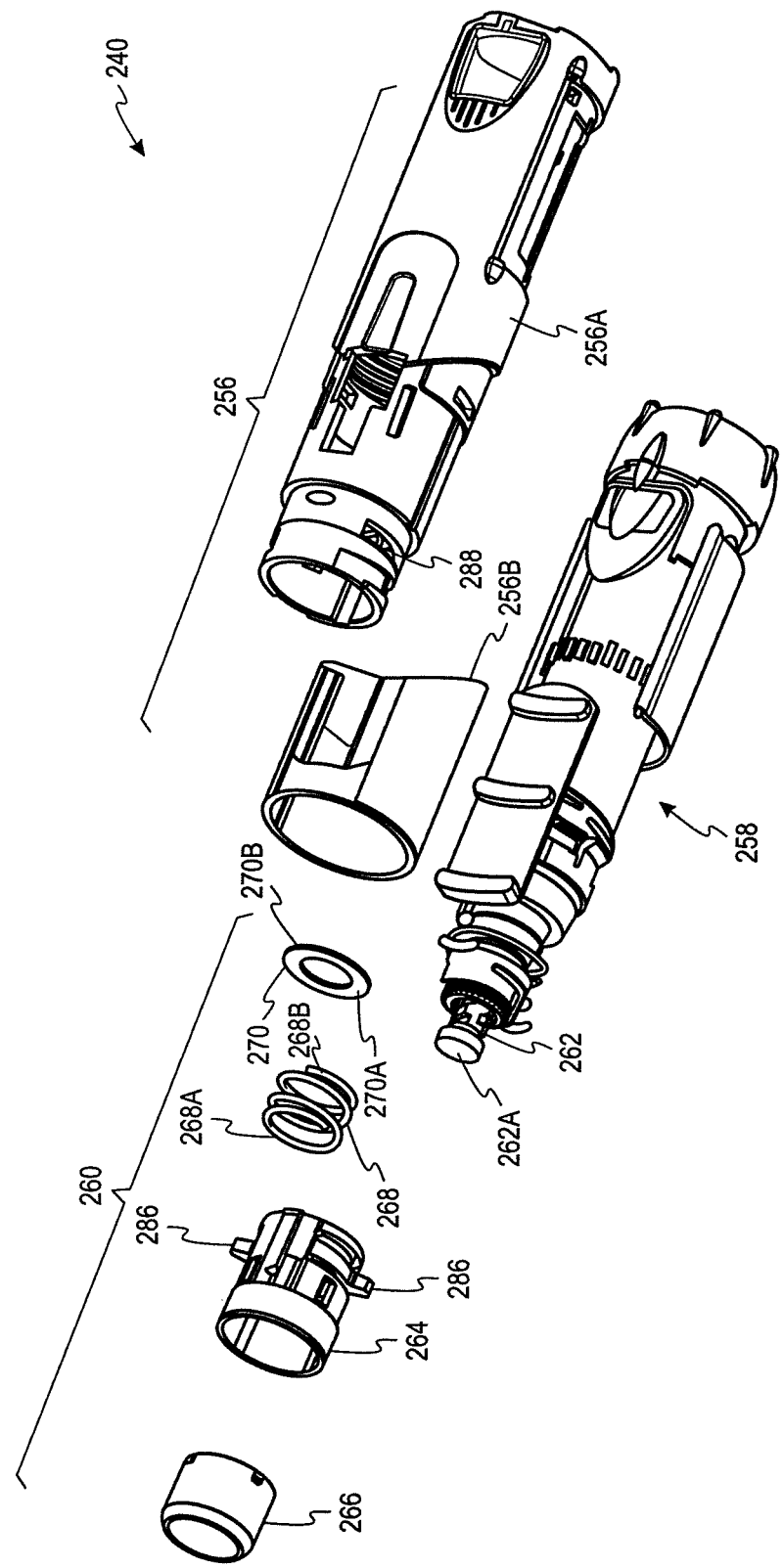
FIG. 12 is an exploded perspective view of an actuator assembly according to aspects of the present disclosure.

FIG. 12 depicts an exploded view of the actuator assembly 240. As shown in FIG. 12, the actuator assembly 240 includes a housing 256, an actuator device 258, and a retainer assembly 260. The housing 256 receives the actuator device 258 and the retainer assembly 260. In FIG. 12, the housing 256 includes a first housing portion 256A that is coupled to a second housing portion 256B to facilitate assembling the actuator assembly 240; however, the housing 256 can be integrally formed and/or include more than two portions in other examples.

The actuator device 258 includes a plunger rod 262 for engaging the stopper 222 in the container 220 when the actuator assembly 240 is coupled to the container holder assembly 210. The plunger rod 262 includes a proximal-most surface 262A for engaging the stopper 222 such that axial movement of the plunger rod 262 causes corresponding axial movement of the stopper 222 within the container 220. The actuator device 258 also includes a drive mechanism (not shown) for axial moving the plunger rod 262 responsive to a user input on the actuator device 258 (e.g., via one or more buttons).

The retainer assembly 260 facilitates positioning the container 220 in a predetermined position within the container holder assembly 210 and with respect to the plunger rod 262 when the actuator assembly 240 is coupled with the container assembly 210. In particular, the retainer assembly 260 applies a proximally directed biasing force to the container 220, which forces the container 220 toward the proximal end 262B of the inner housing 262. Beneficially, the retainer assembly 260 thus allows for relatively undesired tolerances in the physical dimensions of the container 220 and/or container holder assembly 210 without affecting the accuracy of the dose delivery (i.e., by holding the container 220 in a fixed position in relation to the container holder assembly 210, and without damaging the container 220).

Figure 13:
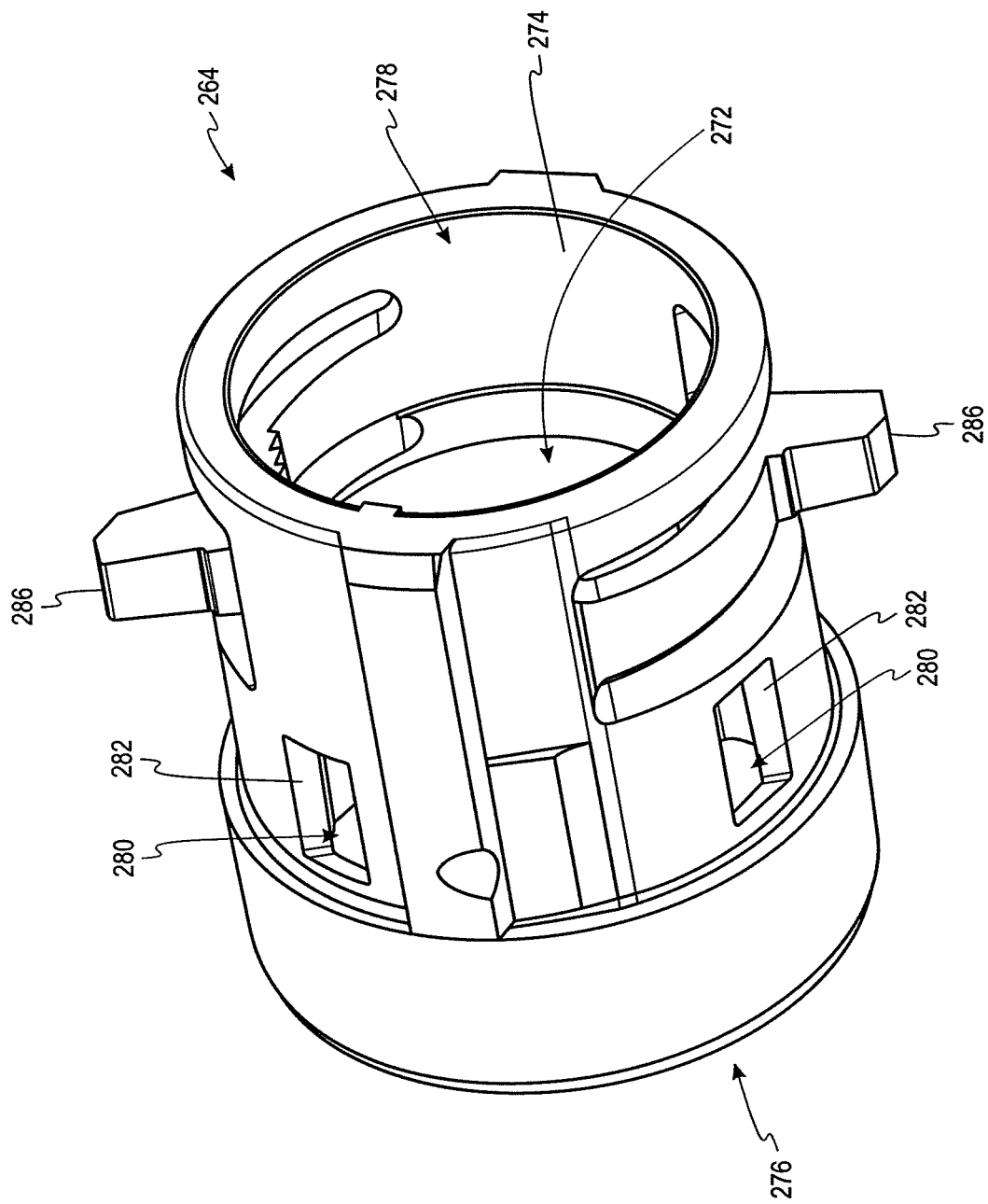
FIG. 13 is a perspective view of a plunger lock according to aspects of the present disclosure.

As shown in FIG. 12, the retainer assembly 260 includes a plunger lock 264, a retaining member 266, a biasing member 268, and a supporting washer 270. A perspective view of the plunger lock 264 is depicted in FIG. 13. As shown in FIG. 13, the plunger lock 264 includes an internal cavity 272 defined by a side wall 274 extending from a proximal opening 276 to a distal opening 278 of the plunger lock 264. Additionally, the plunger lock 264 includes multiple apertures 280 in the side wall 274 of the plunger lock 264. The apertures 280 in the side wall 274 of the plunger lock 264 provide tracks 282 for guiding axial movement of the retaining member 266 as described below.

As shown in FIGS. 8A-8B, the plunger lock 264 is fixedly coupled to the housing 256 of the actuator assembly 240. In particular, when the actuator assembly 240 is assembled, the plunger lock 264 is seated within the proximal portion 228 of the actuator assembly 240. As further shown in FIGS. 8A-8B, when the actuator assembly 240 is assembled, the plunger rod 262 passes through the axially aligned internal cavity 272 of the plunger lock 264. In this way, the plunger rod 262 is secured by the plunger lock 264.

As shown in FIGS. 8A-8B and FIGS. 12-13, the plunger lock 264 also includes one or more retention members 286 extending outwardly away from the side wall 274 of the plunger lock 264. The retention members 286 engage with corresponding apertures 288 in the housing 256 of the actuator assembly 240 to axially retain the plunger lock 264 relative to the housing 256. In the illustrated example, the apertures 288 in the housing 256 extend over a portion of the circumference of the housing 256 to allow the plunger lock 264 to rotate within the housing 256. In other examples, the plunger lock 264 can also be rotationally secured relative to the housing 256.

Figure 14A:
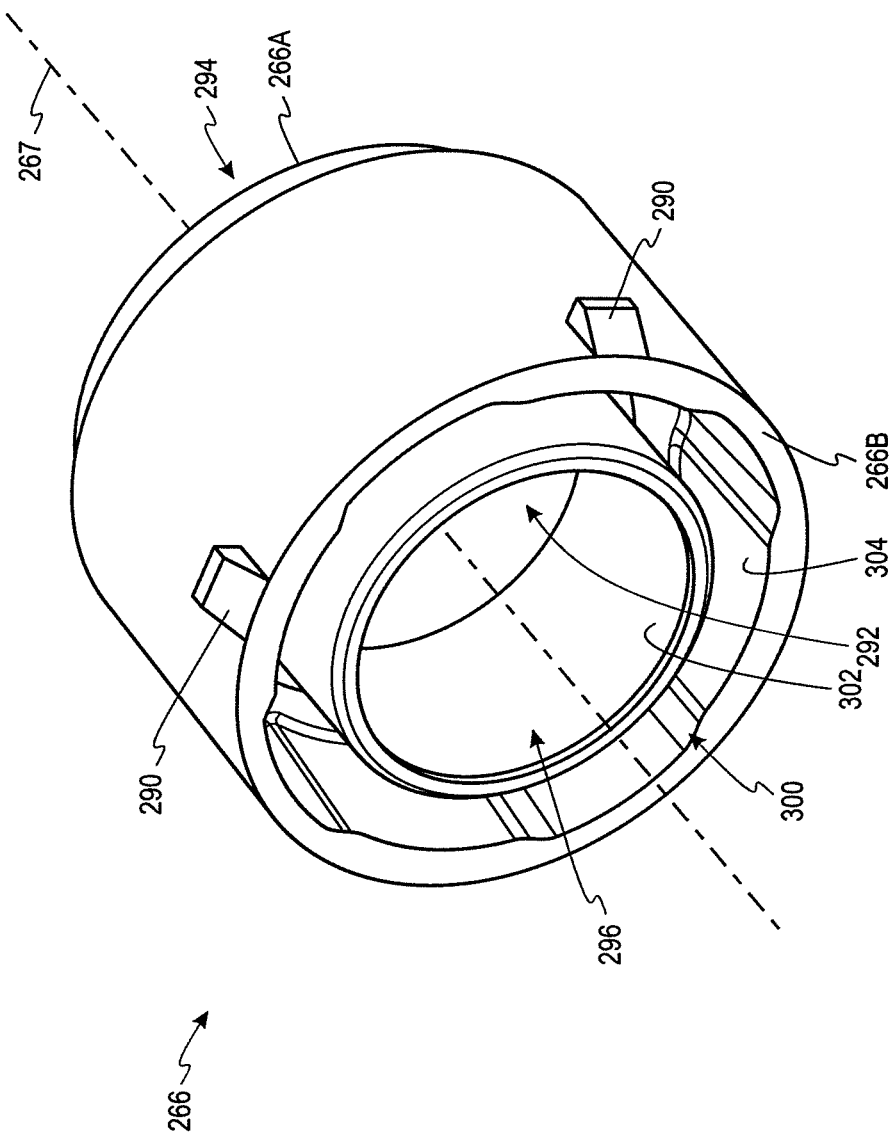
FIGS. 14A-14B are perspective views of a retaining member according to aspects of the present disclosure.
Figure 14B:
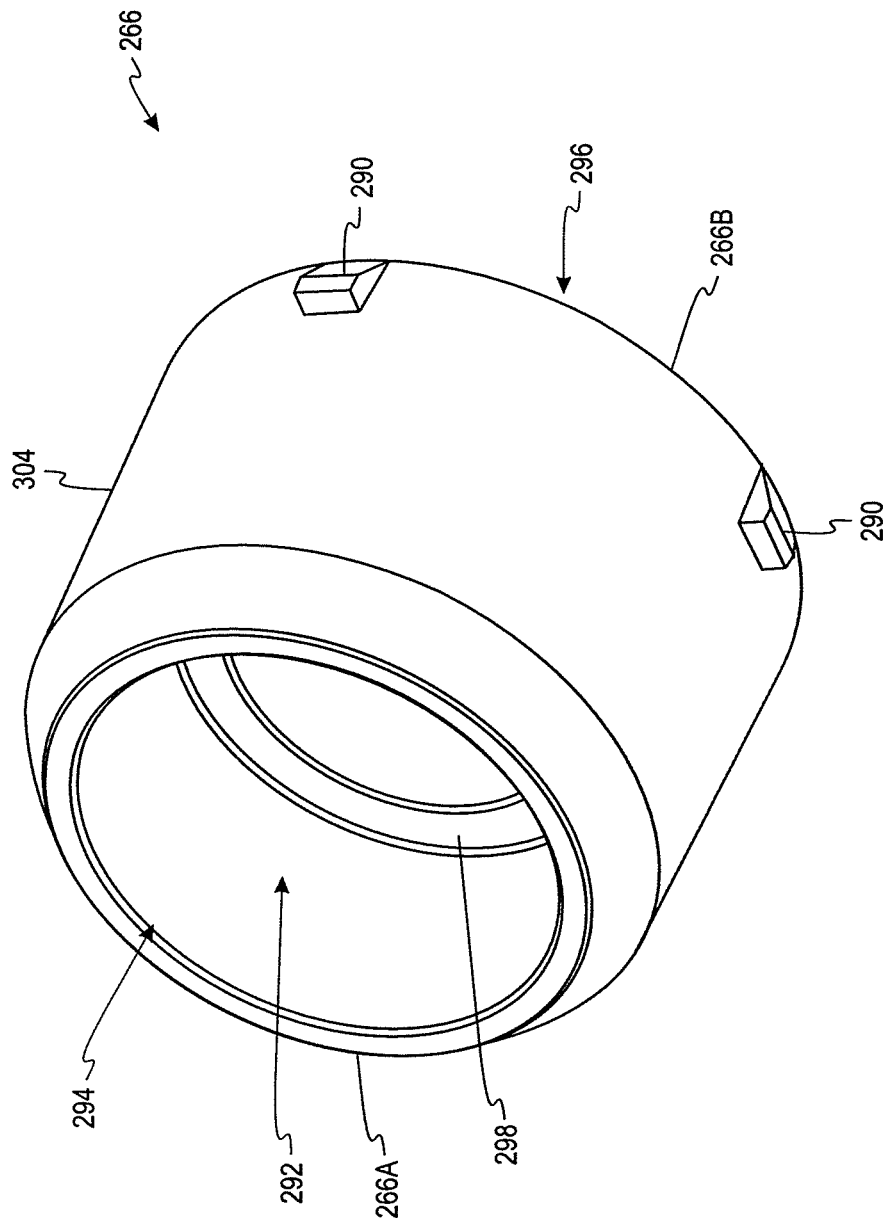
Figure 14C:
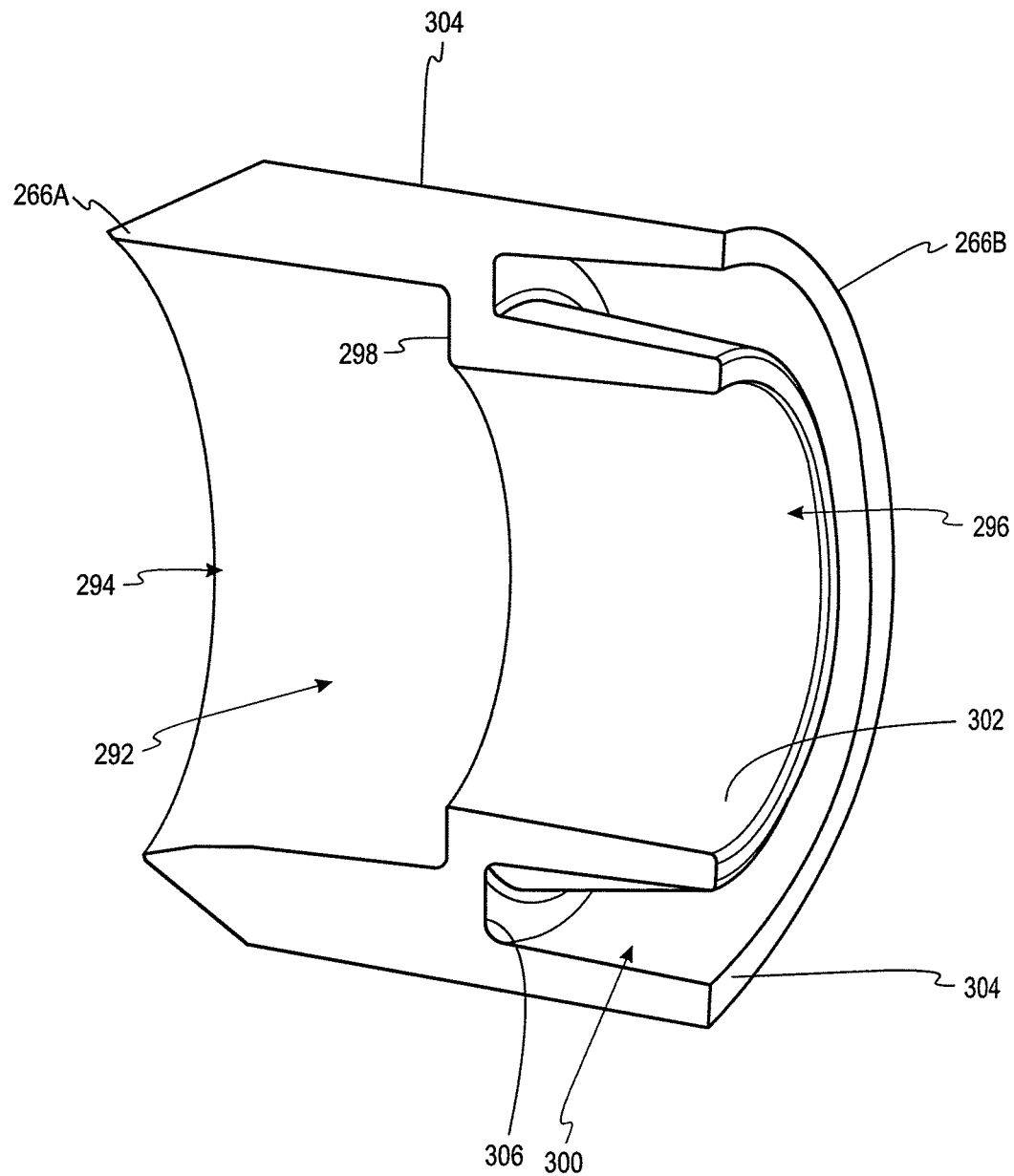
FIG. 14C is a cross-sectional view of the retaining member depicted in FIG. 14A.

FIGS. 14A-14B depict perspective views of the retaining member 266 and FIG. 14C depicts a cross-sectional view of the retaining member 266 taken through an axis 267 in FIG. 14A. As shown in FIGS. 14A-14B, the retaining member 266 has an outer wall 304 that extends from a front end 266A to a back end 266B. The outer wall 304 is generally cylindrical in FIGS. 14A-14C; however, the outer wall 304 can have a different shape in other examples.

On the outer wall 304, the retaining member 266 has a plurality of spacer elements 290 equally spaced around a circumference of the outer wall 304 at the back end 266B of the retaining member 266. Each spacer element 290 is configured to engage a respective one of the tracks 282 on the plunger lock 264 when the retaining member 266 is seated within the internal cavity 272 of the plunger lock 264. When the spacer elements 290 are engaged with the tracks 282, the retaining member 266 can move axially relative to the plunger lock 264 over a predetermined distance corresponding to the length of the tracks 282. In the illustrated example, the engagement between the spacer elements 290 and the tracks 282 can prevent rotational movement of the retaining member 266 relative to the plunger lock 264. In other examples, the spacer elements 290 and/or tracks 282 can be configured to permit rotational movement of the retaining member 266 relative to the plunger lock 264.

Also, as shown in FIGS. 14A-14C, the retaining member 266 includes an interior passage 292 that extends from a proximal opening 294 at the front end 266A to a distal opening 296 at the back end 266B. A first portion of the interior passage 292 extends from the proximal opening 294 to a shoulder 298 and a second portion of the interior passage 292 extends from the shoulder 298 to the distal opening 296. The shoulder 298 provides a first end wall for engaging a distal end of the container 220 when the container 220 is received in the first portion of the interior passage 292. The second portion of the interior passage 292 is configured to receive the plunger rod 262 such that plunger rod 262 can pass through the interior passage 292 and engage the moveable stopper 222 in the container 220. As shown in FIG. 14C, the interior passage 292 generally forms a cylinder in which the first portion of the interior passage 292 has a diameter that is larger than a diameter of the second portion of the interior passage 292.

At the back end 266B, the retaining member 266 further includes a cavity 300 formed between an inner wall 302 and the outer wall 304 of the retaining member 266. The cavity 300 extends from an aperture in the back end 266B to a second end wall 306 in the retaining member 266. The cavity 300 can be cylindrical and, thus, the second end wall 306 can be an annular structure within the retaining member 266. The cavity 300 and the interior passage 292 may also be co-axially aligned with each other. In other examples, the inner wall 302, the outer wall 304, and the cavity 300 can be shaped differently.

Figure 15:
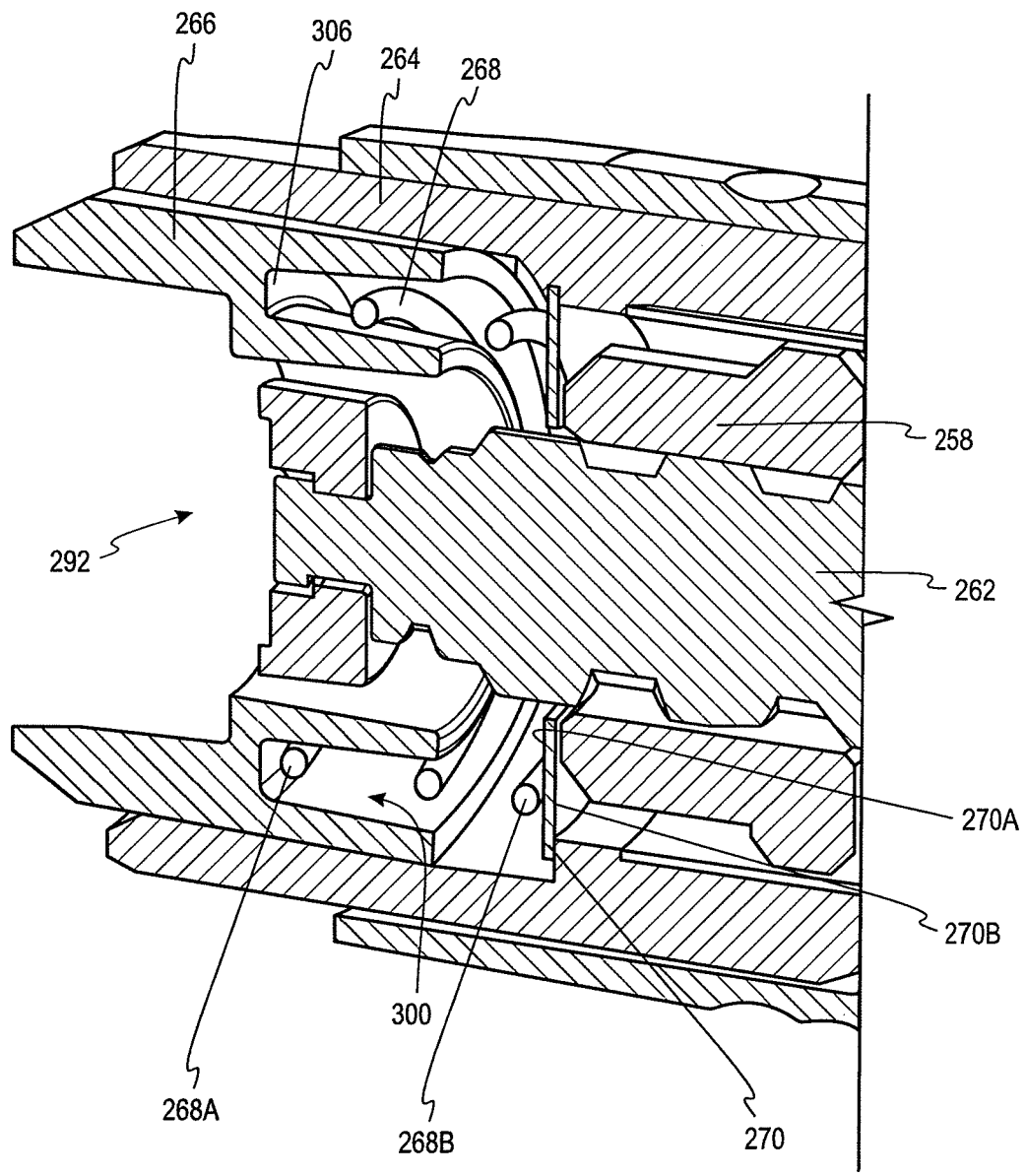
FIG. 15 is a cross-sectional view of a proximal portion of the actuator assembly.

FIG. 15 depicts a cross-sectional view of the proximal end 284 of the actuator assembly 240. As shown in FIG. 15, the cavity 300 receives a first end 268A of the biasing member 268 such that the first end 268A of the biasing member 268 engages the second end wall 306 of the cavity 300. A second end 268B of the biasing member 268 engages a front side 270A of the support washer 270. A back side 270B of the support washer 270 engages a proximal portion of the actuator device 258, inhibiting distal movement of the support washer 270. The biasing member 268 is thus secured between the retaining member 266 and a proximal portion of the actuator device 258. With the support washer 270 axially fixed, the biasing member 268 provides a proximally directed biasing force to the retaining member 266 via the engagement between the biasing member 268 and the second end wall 306. In turn, the retaining member 266 provides the proximally directed biasing force to the container 220 when the container 220 engages the shoulder 298 in the retaining member 266.

Figure 16A:
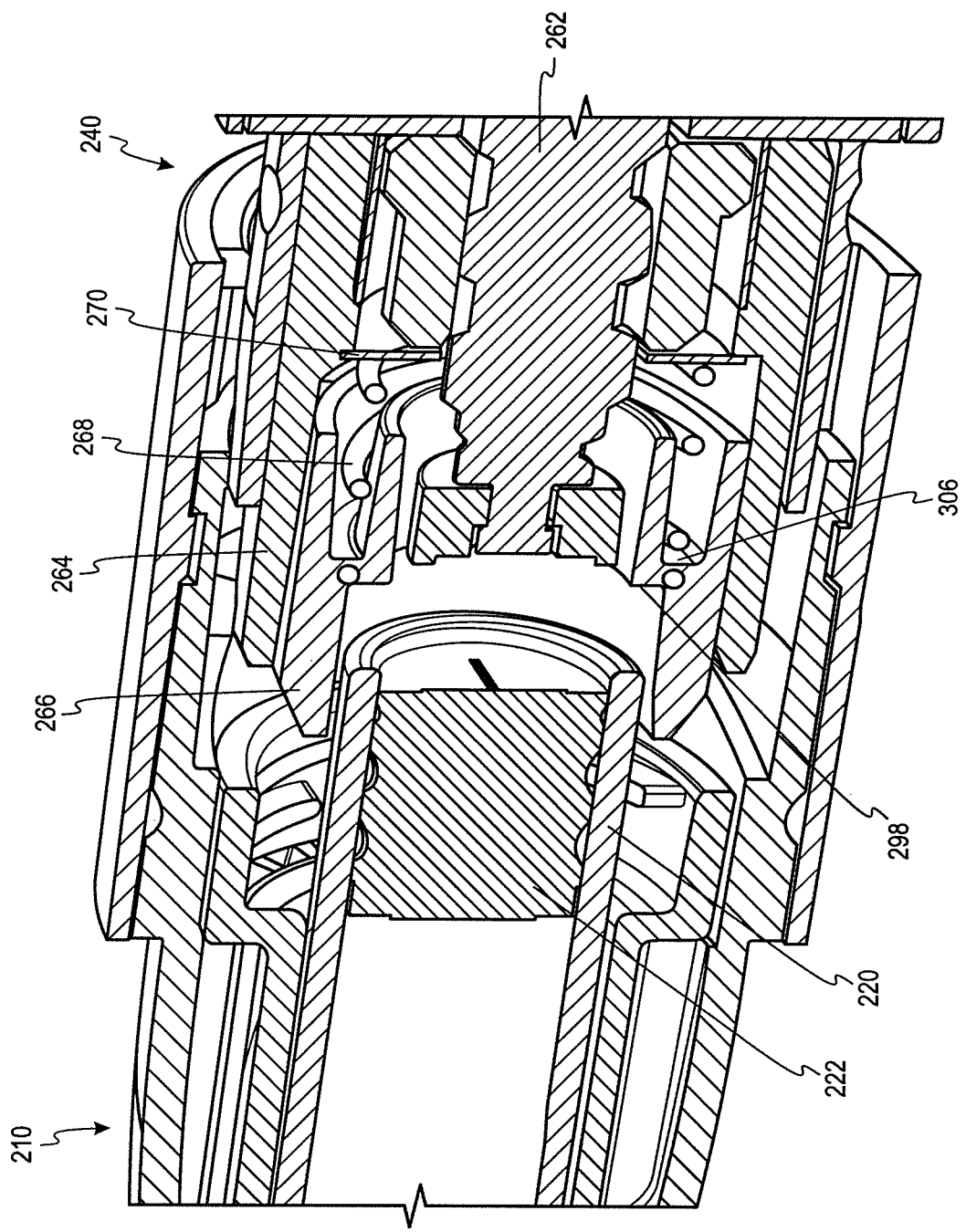
FIG. 16A is a cross-sectional view of the container holder assembly initially engaging the actuator assembly according to aspects of the present disclosure.

As described above, the medicament delivery device 200 is assembled by inserting the container 220 into the bore 214 of the container holder assembly 240. In an example, the container 220 has a length that is generally greater than a length of the bore 214 and, thus, the distal end 218A of the container 220 can extend distally from the distal end 238A of the inner housing 238 (as shown in FIGS. 16A-16B).

Next, the container holder assembly 210 is coupled to the actuator assembly 240. For instance, the protrusions 234 on the inner surface 236 of the container holder assembly 210 can be aligned with the tracks 230 on the exterior surface 226 of the actuator assembly 240. FIG. 16A depicts a cross-sectional view of the container 220 in the interior passage 292 of the retaining member 266 while the container holder assembly 210 initially engages the actuator assembly 240 (e.g., when the protrusion(s) 234 are initially received in the track(s) 230). As shown in FIG. 16A, a distal end of the container 220 extends from the container holder assembly 210 and is received in the first portion of the interior passage 292 of the retaining member 266. In FIG. 16A, with the container holder assembly 210 initially engaging the actuator assembly 240, the container 220 does not yet contact the shoulder 298 in the retaining member 266. Further, the retaining member 266 is biased proximally by the biasing member 268 acting on the second end wall 306 and the supporting washer 270; however, this biasing force is not yet applied to the container 220 because the container 220 does not yet engage the retaining member 266. As described above, the retaining member 266 is axially retained in the plunger lock 264 by the spacer elements 290 of the retaining member 266 engaging the tracks 282 of the plunger lock 264.

The container holder assembly 210 can be further secured to the actuator assembly 240 by rotating the container holder assembly 210 relative to the actuator assembly 240 until the protrusions 234 are fully seated in the tracks 230. FIG. 16B depicts a cross-sectional view of the container 220 in the interior passage 292 of the retaining member 266 after the container holder assembly 210 has been completely coupled to the actuator assembly 240 (e.g., after the container holder assembly 210 has been rotated such that the protrusion(s) 234 reach the end of the track(s) 230). As shown in FIG. 16B, the distal end of the container 220 engages the shoulder 298 of the retaining member 266, forcing the retaining member 266 to an axial position that is distal of the axial position of the retaining member 266 shown in FIG. 16A. Due to this engagement, the retaining member 266 also applies the proximally directed force of the biasing member 268 to the container 220 to facilitate positioning the container 220 in a predetermined position within the container holder assembly 210 (e.g., against the shoulder portion 225 at the proximal end 218B of the container 220).

Figure 16B:
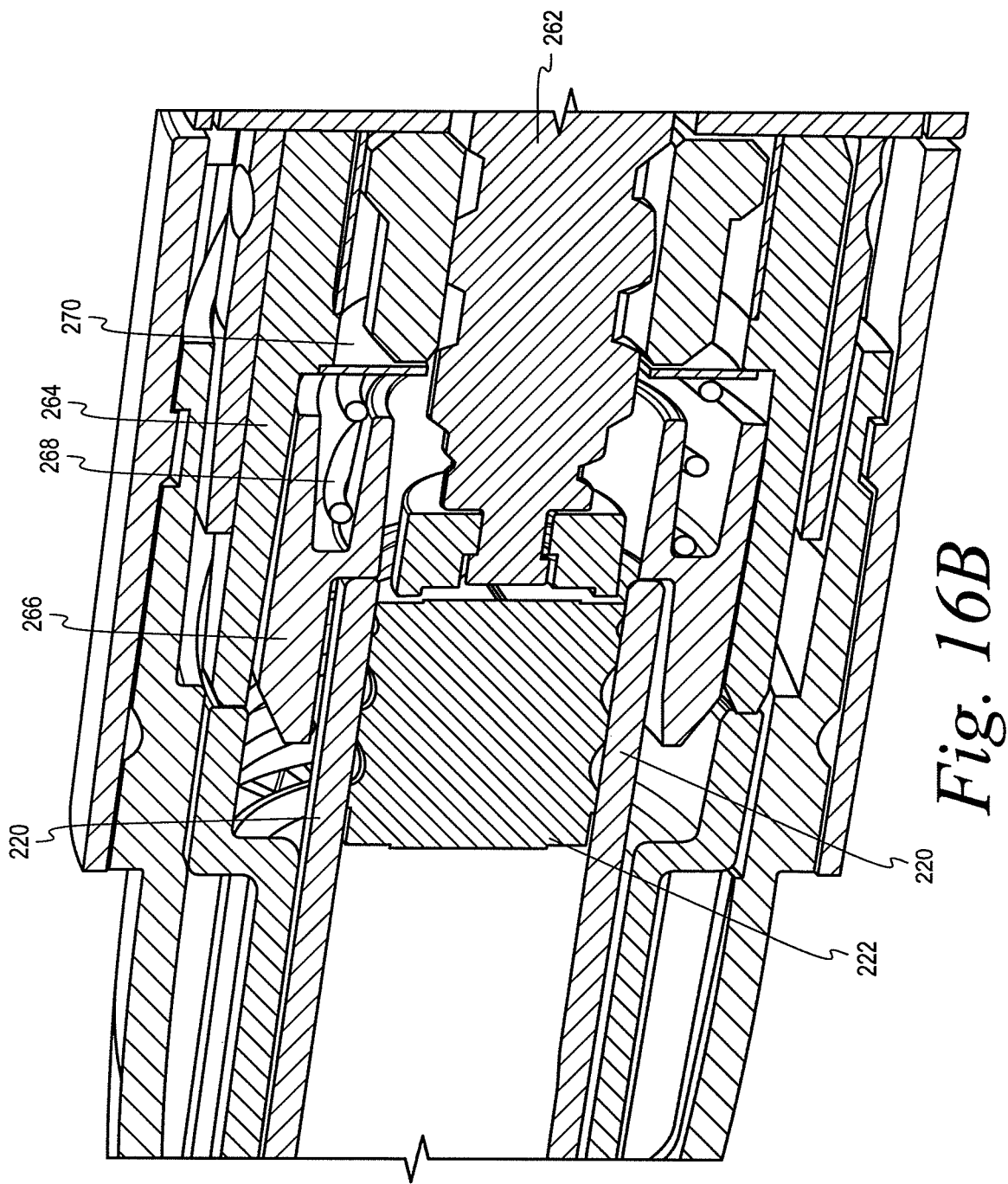
FIG. 16B is a cross-sectional view of the container holder assembly coupled to the actuator assembly according to aspects of the present disclosure.

Further, as shown in FIG. 16B, the plunger rod 262 passes through an aperture in the supporting washer 270, the internal cavity 272 of the plunger lock 264, and the interior passage 292 of the retaining member 266 to engage the movable stopper 222 in the container 220. Additionally, as shown in FIG. 16B, the plunger lock 264 releasably engages the distal end of the container holder assembly 210. In particular, the plunger lock 264 engages the resilient structure 246 on the inner housing 238 of the container holder assembly 210. Due to the resiliency of the resilient structure 246, the inner housing 238 can absorb a proximal force applied by the plunger lock 264 responsive to the container holder assembly 210 coupling to the actuator assembly 240.

The present invention is not limited to the above-described preferred embodiments. Various alternatives, modifications and equivalents may be used. Therefore, the above embodiment should not be taken as limiting the scope of the invention, which is defined by the appended claims.

What is claimed is:

1. A retaining apparatus for use with a medicament delivery device, the medicament delivery device comprising a container holder assembly and an actuator assembly, the container holder assembly configured to receive a container containing a medicament, the container holder assembly configured to couple to the actuator assembly, wherein the actuator assembly comprises a plunger rod for engaging a stopper in the container, the retaining apparatus comprising:
   a plunger lock seated within a proximal end of the actuator assembly, the plunger lock securing the plunger rod;
   a retaining member seated within the plunger lock, wherein the retaining member comprises a cylindrical structure, wherein the cylindrical structure comprises a front end and a back end, wherein the back end of the cylindrical structure comprises an outer wall and an inner wall, wherein the outer wall and the inner wall of the cylindrical structure define a first annular cavity, and wherein the first annular cavity of the cylindrical structure further defines a first annular cavity end wall; and
   a biasing member secured between the proximal end of the actuator assembly and the retaining member, the biasing member having a proximal end and a distal end, wherein the proximal end of the biasing member contacts a distally-facing surface of the retaining member, and wherein the retaining member is biased in a proximal direction by the biasing member.

2. The retaining apparatus of claim 1, wherein the plunger lock defines an internal cavity.

3. The retaining apparatus of claim 2, wherein the retaining member is slidably biased within the internal cavity of the plunger lock.

4. The retaining apparatus of claim 1, wherein the biasing member resides within the first annular cavity of the retaining member and acts upon the first annular cavity end wall to bias the retaining member in the proximal direction.

5. The retaining apparatus of claim 4, further comprising:
   a supporting washer such that the biasing member resides in a biased state between a front side of the supporting washer and the first annular cavity end wall of the retaining member.

6. The retaining apparatus of claim 1, wherein the plunger lock is configured for releasable attachment to a distal end of the container holder assembly.

7. The retaining apparatus of claim 6, wherein the retaining member is configured for releasable attachment to a distal end of the container such that the distal end of the container is resiliently pressed against the container holder assembly.

8. The retaining apparatus of claim 1, wherein the plunger lock is fixedly attached to a housing of the actuator assembly.

9. The retaining apparatus of claim 1, wherein the retaining member comprises a plurality of spacers provided along the outer wall of the cylindrical structure.

10. The retaining apparatus of claim 9, wherein the plurality of spacers are configured to engage a plurality of tracks defined by the plunger lock.

11. The retaining apparatus of claim 10, wherein the plurality of spacers are configured to slidably engage the plurality of tracks defined by the plunger lock.

12. The retaining apparatus of claim 10, wherein the plurality of spacers are configured to allow relative movement of the retaining member with respect to the plunger lock.

13. The retaining apparatus of claim 1, wherein the retaining member is rotatably fixed within the plunger lock.

14. The retaining apparatus of claim 1, wherein the plunger rod passes through an axially aligned aperture defined by the retaining member.

15. The retaining apparatus of claim 1, wherein the plunger rod passes through an axially aligned opening defined by the plunger lock.

16. A retaining apparatus for use with a medicament delivery device, the medicament delivery device comprising a container holder assembly and an actuator assembly, the container holder assembly configured to receive a container containing a medicament, the container holder assembly configured to couple to the actuator assembly, wherein the actuator assembly comprises a plunger rod for engaging a stopper in the container, the retaining apparatus comprising:
- a plunger lock seated within a proximal end of the actuator assembly, the plunger lock securing the plunger rod;
- a retaining member seated within the plunger lock, wherein the retaining member comprises a cylindrical structure, wherein the cylindrical structure comprises a front end and a back end, wherein the back end of the cylindrical structure comprises an outer wall and an inner wall, wherein the outer wall and the inner wall of the cylindrical structure define a first annular cavity, and wherein the front end of the cylindrical structure defines a second annular cavity, the second annular cavity comprising a second end wall that is configured to receive a distal end of the container; and
- a biasing member secured between the proximal end of the actuator assembly and the retaining member, the biasing member having a proximal end and a distal end, wherein the proximal end of the biasing member contacts a distally-facing surface of the retaining member, and
- wherein the retaining member is biased in a proximal direction by the biasing member.

17. A retaining apparatus for use with a medicament delivery device, the medicament delivery device comprising a container holder assembly and an actuator assembly, the container holder assembly configured to receive a container containing a medicament, the container holder assembly configured to couple to the actuator assembly, wherein the actuator assembly comprises a plunger rod for engaging a stopper in the container, the retaining apparatus comprising:
- a plunger lock seated within a proximal end of the actuator assembly, the plunger lock securing the plunger rod;
- a retaining member seated within the plunger lock, wherein the retaining member comprises a plurality of spacers provided along an outer wall of the retaining member, wherein the plurality of spacers are equally spaced along a back end of the retaining member; and
- a biasing member secured between the proximal end of the actuator assembly and the retaining member, the biasing member having a proximal end and a distal end,
- wherein the proximal end of the biasing member contacts a distally-facing surface of the retaining member, and
- wherein the retaining member is biased in a proximal direction by the biasing member.

* * * * *